US011091707B2

(12) United States Patent
Rueter et al.

(10) Patent No.: US 11,091,707 B2
(45) Date of Patent: Aug. 17, 2021

(54) UPGRADED EBULLATED BED REACTOR WITH NO RECYCLE BUILDUP OF ASPHALTENES IN VACUUM BOTTOMS

(71) Applicant: HYDROCARBON TECHNOLOGY & INNOVATION, LLC, Lawrenceville, NJ (US)

(72) Inventors: Michael A. Rueter, Plymouth Meeting, PA (US); David M. Mountainland, Princeton, NJ (US); Brett M. Silverman, Salt Lake City, UT (US); Everette Harris, Ivyland, PA (US)

(73) Assignee: HYDROCARBON TECHNOLOGY & INNOVATION, LLC, Lawrenceville, NJ (US)

( * ) Notice: Subject to any disclaimer, the term of this patent is extended or adjusted under 35 U.S.C. 154(b) by 0 days.

(21) Appl. No.: 16/594,847

(22) Filed: Oct. 7, 2019

(65) Prior Publication Data

US 2020/0115643 A1 Apr. 16, 2020

Related U.S. Application Data

(60) Provisional application No. 62/746,867, filed on Oct. 17, 2018.

(51) Int. Cl.
  *C10G 67/02* (2006.01)
  *C10G 1/00* (2006.01)
  (Continued)

(52) U.S. Cl.
  CPC .............. *C10G 67/02* (2013.01); *B01J 8/005* (2013.01); *B01J 8/0035* (2013.01); *B01J 8/228* (2013.01);
  (Continued)

(58) Field of Classification Search
  None
  See application file for complete search history.

(56) References Cited

U.S. PATENT DOCUMENTS 2,850,552 A  9/1958  Ogle
3,019,180 A  2/1959  Schreiener et al.
(Continued)

FOREIGN PATENT DOCUMENTS

CA  2004882  6/1991
CA  2088402  7/1993
(Continued)

OTHER PUBLICATIONS

U.S. Appl. No. 15/615,574, filed Jun. 6, 2017, Mountainland et al.
(Continued)

*Primary Examiner* — Tam M Nguyen
(74) *Attorney, Agent, or Firm* — Workman Nydegger

(57) ABSTRACT

An ebullated bed hydroprocessing system is upgraded using a dual catalyst system that includes a heterogeneous catalyst and dispersed metal sulfide particles, which permits recycling of vacuum bottoms without recycle buildup of asphaltenes. The dual catalyst system more effectively converts asphaltenes in the ebullated bed reactor and increases asphaltene conversion by an amount that at least offsets higher asphaltene concentration resulting from recycling of vacuum bottoms. In this way, there is no recycle buildup of asphaltenes in upgraded ebullated bed reactor notwithstanding recycling of vacuum bottoms. In addition, residual dispersed metal sulfide catalyst particles in the vacuum bottoms can maintain or increase the concentration of the dispersed metal sulfide catalyst in the ebullated bed reactor.

25 Claims, 16 Drawing Sheets

(51) Int. Cl.
  *B01J 8/22* (2006.01)
  *B01J 8/00* (2006.01)
  *C10G 1/06* (2006.01)
  *C07C 5/09* (2006.01)
  *C07C 7/00* (2006.01)
  *C07C 7/11* (2006.01)
  *C07C 7/12* (2006.01)

(52) U.S. Cl.
  CPC ............... *C07C 5/09* (2013.01); *C07C 7/005* (2013.01); *C07C 7/11* (2013.01); *C07C 7/12* (2013.01); *C10G 1/002* (2013.01); *C10G 1/06* (2013.01); *B01J 2208/00752* (2013.01); *B01J 2208/00805* (2013.01); *C10G 2300/1003* (2013.01); *C10G 2300/1074* (2013.01); *C10G 2300/1077* (2013.01); *C10G 2300/206* (2013.01); *C10G 2300/208* (2013.01); *C10G 2300/301* (2013.01); *C10G 2300/4056* (2013.01); *C10G 2300/4075* (2013.01); *C10G 2300/4081* (2013.01); *C10G 2300/70* (2013.01)

(56) References Cited

U.S. PATENT DOCUMENTS

| | | |
|---|---|---|
| 3,161,585 A | 12/1964 | Gleim et al. |
| 3,254,017 A | 5/1966 | Arey, Jr. et al. |
| 3,267,021 A | 8/1966 | Gould |
| 3,297,563 A | 1/1967 | Doumani |
| 3,349,713 A | 10/1967 | Fassbender |
| 3,362,972 A | 1/1968 | Kollar |
| 3,578,690 A | 5/1971 | Becker |
| 3,595,891 A | 7/1971 | Cavitt |
| 3,622,497 A | 11/1971 | Gleim |
| 3,622,498 A | 11/1971 | Stolfa et al. |
| 3,694,351 A | 9/1972 | White |
| 3,694,352 A | 9/1972 | Gleim |
| 3,816,020 A | 6/1974 | Ogles |
| 3,870,623 A | 3/1975 | Johnson et al. |
| 3,892,389 A | 7/1975 | Contastin |
| 3,915,842 A | 10/1975 | Gatsis |
| 3,919,074 A | 11/1975 | Gatsis |
| 3,953,362 A | 4/1976 | Lines et al. |
| 3,983,028 A | 9/1976 | McCollum et al. |
| 3,992,285 A | 11/1976 | Hutchings |
| 4,022,681 A | 5/1977 | Sheng et al. |
| 4,066,530 A | 1/1978 | Aldridge et al. |
| 4,066,561 A | 1/1978 | Nnadi |
| 4,067,798 A | 1/1978 | Hauschildt et al. |
| 4,067,799 A | 1/1978 | Bearden, Jr. et al. |
| 4,068,830 A | 1/1978 | Gray |
| 4,077,867 A | 3/1978 | Aldridge et al. |
| 4,083,803 A | 4/1978 | Oswald et al. |
| 4,125,455 A | 11/1978 | Herbstman |
| 4,134,825 A | 1/1979 | Bearden, Jr. et al. |
| 4,148,750 A | 4/1979 | Pine |
| 4,151,070 A | 4/1979 | Allan et al. |
| 4,169,038 A | 9/1979 | Metrailer et al. |
| 4,178,227 A | 12/1979 | Metrailer et al. |
| 4,181,601 A | 1/1980 | Sze |
| 4,191,636 A | 3/1980 | Ando et al. |
| 4,192,735 A | 3/1980 | Aldridge et al. |
| 4,196,072 A | 4/1980 | Aldridge et al. |
| 4,226,742 A | 10/1980 | Bearden, Jr. et al. |
| 4,252,634 A | 2/1981 | Khulbe et al. |
| 4,285,804 A | 8/1981 | Jacquin et al. |
| 4,298,454 A | 11/1981 | Aldridge et al. |
| 4,305,808 A | 12/1981 | Bowes |
| 4,313,818 A | 2/1982 | Aldridge et al. |
| 4,325,802 A | 4/1982 | Porter et al. |
| 4,338,183 A | 7/1982 | Gatsis |
| 4,352,729 A | 10/1982 | Jacquin et al. |
| 4,370,221 A | 1/1983 | Patmore et al. |
| 4,389,301 A | 6/1983 | Dahlberg et al. |
| 4,411,768 A | 10/1983 | Unger et al. |
| 4,420,008 A | 12/1983 | Shu |
| 4,422,927 A | 12/1983 | Kowalczyk et al. |
| 4,422,960 A | 12/1983 | Shiroto et al. |
| 4,427,532 A | 1/1984 | Varghese |
| 4,430,207 A | 2/1984 | Kukes |
| 4,435,314 A | 3/1984 | van de Leemput et al. |
| 4,452,265 A | 6/1984 | Lonnebring |
| 4,454,023 A | 6/1984 | Lutz |
| 4,455,218 A | 6/1984 | Dymock et al. |
| 4,457,831 A | 7/1984 | Gendler |
| 4,465,630 A | 8/1984 | Akashi et al. |
| 4,467,049 A | 8/1984 | Yoshii et al. |
| 4,485,004 A | 11/1984 | Fisher et al. |
| 4,485,008 A | 11/1984 | Maa et al. |
| 4,508,616 A | 4/1985 | Larrauri et al. |
| 4,513,098 A | 4/1985 | Tsao |
| 4,551,230 A | 11/1985 | Kukes et al. |
| 4,557,823 A | 12/1985 | Kukes et al. |
| 4,557,824 A | 12/1985 | Kukes et al. |
| 4,561,964 A | 12/1985 | Singhal et al. |
| 4,564,441 A | 1/1986 | Kukes et al. |
| 4,567,156 A | 1/1986 | Bearden, Jr. et al. |
| 4,568,657 A | 2/1986 | Sepulveda et al. |
| 4,578,181 A | 3/1986 | Derouane et al. |
| 4,579,646 A | 4/1986 | Grosboll et al. |
| 4,581,344 A | 4/1986 | Ledoux et al. |
| 4,582,432 A | 4/1986 | Mehta |
| 4,585,545 A | 4/1986 | Yancey, Jr. et al. |
| 4,590,172 A | 5/1986 | Isaacs |
| 4,592,827 A | 6/1986 | Galiasso et al. |
| 4,592,830 A | 6/1986 | Howell et al. |
| 4,606,809 A | 8/1986 | Garg |
| 4,608,152 A | 8/1986 | Howell et al. |
| 4,613,427 A | 9/1986 | Sepulveda et al. |
| 4,614,726 A | 9/1986 | Walter |
| 4,626,340 A | 12/1986 | Galiasso et al. |
| 4,633,001 A | 12/1986 | Cells |
| 4,652,311 A | 3/1987 | Gulla et al. |
| 4,652,647 A | 3/1987 | Schlosberg et al. |
| 4,674,885 A | 6/1987 | Erwin et al. |
| 4,676,886 A | 6/1987 | Rahbe et al. |
| 4,678,557 A | 7/1987 | Rodriguez et al. |
| 4,693,991 A | 9/1987 | Bjornson et al. |
| 4,695,369 A | 9/1987 | Garg et al. |
| 4,701,435 A | 10/1987 | Garcia et al. |
| 4,707,245 A | 11/1987 | Baldasarri et al. |
| 4,707,246 A | 11/1987 | Gardner et al. |
| 4,710,486 A | 12/1987 | Lopez et al. |
| 4,713,167 A | 12/1987 | Reno et al. |
| 4,716,142 A | 12/1987 | Laine et al. |
| 4,724,069 A | 2/1988 | Aldag et al. |
| 4,734,186 A | 3/1988 | Parrott et al. |
| 4,740,295 A | 4/1988 | Bearden, Jr. et al. |
| 4,746,419 A | 5/1988 | Peck et al. |
| 4,762,607 A | 8/1988 | Aldridge et al. |
| 4,762,812 A | 8/1988 | Lopez et al. |
| 4,762,814 A | 8/1988 | Parrott et al. |
| 4,764,266 A | 8/1988 | Chen et al. |
| 4,765,882 A | 8/1988 | Aldridge et al. |
| 4,770,764 A | 9/1988 | Ohtake et al. |
| 4,772,378 A | 9/1988 | Miyauchi et al. |
| 4,772,387 A | 9/1988 | Simoni |
| 4,802,972 A | 2/1989 | Kukes et al. |
| 4,808,007 A | 2/1989 | King |
| 4,812,228 A | 3/1989 | Angevine et al. |
| 4,824,611 A | 4/1989 | Cells |
| 4,824,821 A | 4/1989 | Lopez et al. |
| 4,834,865 A | 5/1989 | Kukes et al. |
| 4,837,193 A | 6/1989 | Akizuki et al. |
| 4,851,107 A | 7/1989 | Kretschmar et al. |
| 4,851,109 A | 7/1989 | Chen et al. |
| 4,857,496 A | 8/1989 | Lopez et al. |
| 4,859,309 A | 8/1989 | De Vries et al. |
| 4,863,887 A | 9/1989 | Ohtake et al. |
| 4,959,140 A | 9/1990 | Kukes et al. |
| 4,963,247 A | 10/1990 | Belinko et al. |
| 4,970,190 A | 11/1990 | Lopez et al. |

(56) References Cited

U.S. PATENT DOCUMENTS

| | | |
|---|---|---|
| 4,983,273 A | 1/1991 | Kennedy et al. |
| 4,983,558 A | 1/1991 | Born et al. |
| 5,013,427 A | 5/1991 | Mosby et al. |
| 5,017,535 A | 5/1991 | Schoonhoven et al. |
| 5,017,712 A | 5/1991 | Usui et al. |
| 5,038,392 A | 8/1991 | Morris et al. |
| 5,039,392 A | 8/1991 | Bearden, Jr. et al. |
| 5,055,174 A | 10/1991 | Howell et al. |
| 5,080,777 A | 1/1992 | Aegerter et al. |
| 5,094,991 A | 3/1992 | Lopez et al. |
| 5,108,581 A | 4/1992 | Aldridge et al. |
| 5,114,900 A | 5/1992 | King |
| 5,134,108 A | 7/1992 | Thakur et al. |
| 5,154,818 A | 10/1992 | Harandi et al. |
| 5,162,282 A | 11/1992 | Lopez et al. |
| 5,164,075 A | 11/1992 | Lopez |
| 5,166,118 A | 11/1992 | Kretschmar et al. |
| 5,171,916 A | 12/1992 | Le et al. |
| 5,178,749 A | 1/1993 | Lopez et al. |
| 5,191,131 A | 3/1993 | Takahata et al. |
| 5,254,240 A | 10/1993 | Jacquin et al. |
| 5,281,328 A | 1/1994 | Degnan, Jr. et al. |
| 5,320,500 A | 6/1994 | Cholet |
| 5,332,489 A | 7/1994 | Veluswamy |
| 5,332,709 A | 7/1994 | Nappier et al. |
| 5,358,634 A | 10/1994 | Rankel |
| 5,364,524 A | 11/1994 | Partridge et al. |
| 5,372,705 A | 12/1994 | Bhattacharya et al. |
| 5,374,348 A | 12/1994 | Sears et al. |
| 5,409,595 A | 4/1995 | Harandi et al. |
| 5,435,908 A | 7/1995 | Nelson et al. |
| 5,452,954 A | 9/1995 | Handke et al. |
| 5,460,714 A | 10/1995 | Fixari et al. |
| 5,474,977 A | 12/1995 | Gatsis |
| 5,578,197 A | 11/1996 | Cyr et al. |
| 5,597,236 A | 1/1997 | Fasano |
| 5,622,616 A | 4/1997 | Porter et al. |
| 5,865,537 A | 2/1999 | Streiff et al. |
| 5,866,501 A | 2/1999 | Pradhan et al. |
| 5,868,923 A | 2/1999 | Porter et al. |
| 5,871,638 A | 2/1999 | Pradhan et al. |
| 5,913,324 A | 6/1999 | Signer |
| 5,916,432 A | 6/1999 | McFarlane et al. |
| 5,925,235 A | 7/1999 | Habib |
| 5,932,090 A | 8/1999 | Marchionna et al. |
| 5,935,419 A | 8/1999 | Khan et al. |
| 5,954,945 A | 9/1999 | Cayton et al. |
| 5,962,364 A | 10/1999 | Wilson, Jr. et al. |
| 5,972,202 A | 10/1999 | Benham et al. |
| 6,004,453 A | 12/1999 | Benham et al. |
| 6,059,957 A | 5/2000 | Khan et al. |
| 6,068,758 A | 5/2000 | Strausz |
| 6,086,749 A | 7/2000 | Kramer et al. |
| 6,090,858 A | 7/2000 | El-Sayed |
| 6,093,824 A | 7/2000 | Reichle et al. |
| 6,136,179 A | 10/2000 | Sherwood, Jr. et al. |
| 6,139,723 A | 10/2000 | Pelrine et al. |
| 6,190,542 B1 | 2/2001 | Comolliea et al. |
| 6,214,195 B1 | 4/2001 | Yadav et al. |
| 6,217,746 B1 | 4/2001 | Thakkar et al. |
| 6,239,054 B1 | 5/2001 | Shukis et al. |
| 6,270,654 B1 | 8/2001 | Colyar et al. |
| 6,274,530 B1 | 8/2001 | Cayton et al. |
| 6,277,270 B1 | 8/2001 | Morel et al. |
| 6,309,537 B1 | 10/2001 | Harle et al. |
| 6,342,224 B1 | 1/2002 | Bruck et al. |
| 6,379,532 B1 | 4/2002 | Hoehn et al. |
| 6,454,932 B1 | 9/2002 | Baldassari et al. |
| 6,455,594 B1 | 9/2002 | Tsuji |
| 6,462,095 B1 | 10/2002 | Bonsel et al. |
| 6,550,960 B2 | 4/2003 | Catalfamo et al. |
| 6,596,155 B1 | 7/2003 | Gates et al. |
| 6,660,157 B2 | 12/2003 | Que et al. |
| 6,686,308 B2 | 2/2004 | Mao et al. |
| 6,698,197 B1 | 3/2004 | Peterson |
| 6,698,917 B2 | 3/2004 | Etchells, III et al. |
| 6,712,955 B1 | 3/2004 | Hou et al. |
| 6,783,661 B1 | 8/2004 | Briot et al. |
| 6,797,153 B1 | 9/2004 | Fukuyama et al. |
| 6,884,340 B1 | 4/2005 | Bogdan |
| 6,916,762 B2 | 7/2005 | Shibuya et al. |
| 7,011,807 B2 | 3/2006 | Zhou et al. |
| 7,090,767 B2 | 8/2006 | Kaminsky et al. |
| 7,285,698 B2 | 10/2007 | Liu et al. |
| 7,449,103 B2 | 11/2008 | Lott et al. |
| 7,517,446 B2 | 4/2009 | Lott et al. |
| 7,578,928 B2 | 8/2009 | Lott et al. |
| 7,670,984 B2 | 3/2010 | Wu et al. |
| 7,815,870 B2 | 10/2010 | Lott et al. |
| 7,842,635 B2 | 11/2010 | Zhou et al. |
| 7,951,745 B2 | 5/2011 | Zhou et al. |
| 8,034,232 B2 | 10/2011 | Lott et al. |
| 8,142,645 B2 | 3/2012 | Zhou et al. |
| 8,303,082 B2 | 11/2012 | Lott et al. |
| 8,303,802 B2 | 11/2012 | Lott et al. |
| 8,309,041 B2 | 11/2012 | Lott et al. |
| 8,557,105 B2 | 3/2013 | Lott et al. |
| 8,431,016 B2 | 4/2013 | Lott et al. |
| 8,435,400 B2 | 5/2013 | Kou et al. |
| 8,440,071 B2 | 5/2013 | Lott et al. |
| 8,445,399 B2 | 5/2013 | Wu et al. |
| 8,673,130 B2 | 3/2014 | Lott et al. |
| 9,605,215 B2 | 3/2017 | Lott et al. |
| 9,644,157 B2 | 5/2017 | Harris et al. |
| 2002/0125172 A1 | 9/2002 | Que et al. |
| 2002/0179493 A1 | 12/2002 | Etter |
| 2003/0094400 A1 | 5/2003 | Levy et al. |
| 2003/0171207 A1 | 9/2003 | Shih et al. |
| 2004/0013601 A1 | 1/2004 | Butz et al. |
| 2004/0147618 A1 | 7/2004 | Lee et al. |
| 2005/0109674 A1 | 5/2005 | Klein |
| 2005/0241991 A1 | 11/2005 | Lott et al. |
| 2005/0241992 A1 | 11/2005 | Lott et al. |
| 2005/0241993 A1 | 11/2005 | Lott et al. |
| 2005/0258073 A1 | 11/2005 | Oballa et al. |
| 2005/0279670 A1 | 12/2005 | Long et al. |
| 2006/0060501 A1 | 3/2006 | Gauthier |
| 2006/0079396 A1 | 4/2006 | Saito |
| 2006/0175229 A1 | 8/2006 | Montanari et al. |
| 2006/0201854 A1 | 9/2006 | Lott et al. |
| 2006/0224000 A1 | 10/2006 | Papp et al. |
| 2006/0254956 A1 | 11/2006 | Khan |
| 2006/0289340 A1 | 12/2006 | Brownscombe et al. |
| 2007/0012595 A1 | 1/2007 | Brownscombe et al. |
| 2007/0029228 A1 | 2/2007 | Aoki et al. |
| 2007/0108100 A1 | 5/2007 | Satchell, Jr. |
| 2007/0131587 A1 | 6/2007 | Fukuyama et al. |
| 2007/0138059 A1 | 6/2007 | Farshid et al. |
| 2007/0158236 A1 | 7/2007 | Zhou et al. |
| 2007/0158238 A1 | 7/2007 | Wu et al. |
| 2007/0158239 A1 | 7/2007 | Satchell |
| 2007/0163921 A1 | 7/2007 | Keusenkothen et al. |
| 2007/0175797 A1 | 8/2007 | Iki et al. |
| 2007/0209965 A1 | 9/2007 | Duddy et al. |
| 2008/0107881 A1 | 5/2008 | Nakashiba et al. |
| 2009/0107881 A1 | 4/2009 | Lott et al. |
| 2009/0152165 A1 | 6/2009 | Etter |
| 2009/0159505 A1 | 6/2009 | Da Costa et al. |
| 2009/0173666 A1 | 7/2009 | Zhou et al. |
| 2009/0308792 A1 | 12/2009 | Wu et al. |
| 2009/0310435 A1 | 12/2009 | Lott et al. |
| 2010/0065472 A1 | 3/2010 | Chabot |
| 2010/0122931 A1 | 5/2010 | Zimmerman et al. |
| 2010/0294701 A1 | 11/2010 | Lott et al. |
| 2011/0017637 A1 | 1/2011 | Reynolds et al. |
| 2011/0017641 A1 | 1/2011 | Gupta et al. |
| 2012/0152805 A1 | 6/2012 | Chabot |
| 2013/0068658 A1 | 3/2013 | Lott et al. |
| 2013/0068858 A1 | 3/2013 | Nuzzo et al. |
| 2013/0075304 A1 | 3/2013 | Chang et al. |
| 2013/0228494 A1 | 9/2013 | Lott et al. |
| 2013/0233765 A1 | 9/2013 | Lott et al. |
| 2014/0027344 A1 | 1/2014 | Harris |
| 2014/0093433 A1 | 4/2014 | Lott et al. |

(56) References Cited

U.S. PATENT DOCUMENTS

| | | | |
|---|---|---|---|
| 2014/0291203 | A1 | 10/2014 | Molinari et al. |
| 2015/0361360 | A1 | 12/2015 | Harris et al. |
| 2017/0066978 | A1 | 3/2017 | Lott et al. |
| 2017/0081599 | A1 | 3/2017 | Mountainland et al. |
| 2017/0081600 | A1 | 3/2017 | Mountainland et al. |

FOREIGN PATENT DOCUMENTS

| | | | |
|---|---|---|---|
| CA | 1295112 | | 5/2001 |
| CA | 1966618 | | 5/2007 |
| CA | 2579528 | | 9/2007 |
| CN | 1219570 | | 6/1999 |
| CN | 1295112 | A | 5/2001 |
| CN | 1448482 | | 10/2003 |
| CN | 2579528 | Y | 10/2003 |
| CN | 1933766 | A | 3/2007 |
| CN | 1950484 | | 4/2007 |
| CN | 101015440 | A | 8/2007 |
| CN | 202960636 | U | 6/2013 |
| CN | 103228355 | A | 7/2013 |
| CN | 104349804 | A | 2/2015 |
| CN | 104560158 | A | 4/2015 |
| CN | 105518109 | A | 4/2016 |
| CN | 106535954 | A | 3/2017 |
| CN | 108531215 | A | 9/2018 |
| CN | 108699451 | A | 10/2018 |
| DE | 2324441 | | 12/1973 |
| DE | 2315114 | | 10/1974 |
| DE | 2421934 | | 11/1974 |
| EP | 0199399 | | 10/1986 |
| EP | 0546686 | | 7/1993 |
| EP | 0559399 | | 9/1993 |
| EP | 0753846 | A1 | 1/1997 |
| EP | 1043069 | | 10/2000 |
| EP | 1753846 | | 2/2007 |
| EP | 2811006 | A1 | 12/2014 |
| EP | 3369801 | A1 | 9/2018 |
| GB | 1047698 | | 8/1963 |
| JP | 47014205 | | 10/1972 |
| JP | 59108091 | | 6/1984 |
| JP | 5950276 | | 12/1984 |
| JP | 60044587 | | 3/1985 |
| JP | 6239634 | | 8/1987 |
| JP | 6327596 | | 2/1988 |
| JP | 01-165692 | A | 6/1989 |
| JP | 2001165692 | | 6/1989 |
| JP | 2863858 | | 2/1990 |
| JP | 5501829 | | 4/1993 |
| JP | 06009966 | | 1/1994 |
| JP | 06287574 | | 10/1994 |
| JP | 06346064 | | 12/1994 |
| JP | 07062355 | | 3/1995 |
| JP | 0790282 | | 4/1995 |
| JP | 08325580 | | 12/1996 |
| JP | 2000502146 | | 2/2000 |
| JP | 2003193074 | | 7/2003 |
| JP | 2007-535604 | A | 12/2007 |
| JP | 2011502204 | | 1/2011 |
| JP | 2015-527452 | A | 9/2015 |
| RU | 2181751 | C2 | 4/2002 |
| WO | 199723582 | | 12/1996 |
| WO | 199734967 | | 3/1997 |
| WO | 1997029841 | | 8/1997 |
| WO | 00/01408 | A2 | 1/2000 |
| WO | 200075336 | | 12/2000 |
| WO | 200101408 | | 1/2001 |
| WO | 200141799 | | 6/2001 |
| WO | 2005104749 | | 11/2005 |
| WO | 2005104752 | | 11/2005 |
| WO | 2006116913 | | 11/2006 |
| WO | 2007078622 | | 7/2007 |
| WO | 2007106783 | | 9/2007 |
| WO | 2008/151792 | A1 | 12/2008 |
| WO | 2008/151972 | A2 | 12/2008 |
| WO | 2009058785 | | 5/2009 |
| WO | 2010033487 | | 3/2010 |
| WO | 2017053117 | | 3/2017 |

OTHER PUBLICATIONS

Aspen Hydrocracker™: A simulation system for monitoring, planning and optimizing hydrocracking and hydrotreating units, www.aspentec.com/brochures/hydrocracker.pdf (2001).

Criterion: Hydrocracking Process Description and Criterion/Zeolyst Hydrocracking Catalyst Applications, www.criterioncatalysts.com (2001).

Database CA [online] Chemical Abstracts Service retrieved from STN Database accession No. 1991:42412.

Del Bianco et al. "Upgrading Heavy Oil Using Slurry Processes" Chemtech, Nov. 30, 1995 (Nov. 30, 1995), pp. 35-43.

Hawley's Condensed Chemical Dictionary, Richard J. Lewis, Sr. 15 Edition, 2007, p. 321.

"HYVAHL, Significantly Improved RFCC Performance or Low Sulfur Fuel Oils Via Residue Hydrotreatment", Axens IPF Group Technologies, pp. 1,2 (Jan. 2003).

Lott et al.: "(HC)3 Process—A Slurry Hydrocracking Technology Designed to Convert Bottoms of Heavy Oils" 7th UNITAR International Conference of Heavy Crude and Tar Sands, Beijing, Oct. 27, 1998 (Oct. 27, 1998) pp. 1-8.

McFarlane et al. "Dispersion and Activity of Inorganic Catalyst Precursor in Heavy Oil" Boston Congress ACS Energy and Fuel Diversification, p. 496, Aug. 31, 1998.

Molecular Profile Report, Cobalt Benzoate, http://chemfinder.cambridgesoft.com/chembiofinder/forms/search/contentarea/chembiovizsearch.aspx?formgroupid=8&appname=chembiofinder&allowfullsearch=true&keeprecordcount synchronized-flase&searchcriteraid=47searchcriteravalue=932-69-4&currentindex=0.

"OCR Moving Bed Technology for the future", pp. 1-2 (at least as early as 2004).

Panariti et al.: "Petroleum Residue Upgrading with Dispered Catalysts Part 1. Catalysts Activity and Selctivity" Applied Catalysts A: General, vol. 204, Mar. 31, 2000 (Mar. 1, 2000) pp. 203-213.

Panariti et al.: "Petroleum Residue Upgrading with Dispersed Catalysts Part 2. Effect of Operating Conditions" Applied Catalysts A: General, vol. 204, Mar. 31, 2000 (Mar. 1, 2000) pp. 215-222.

Papaioannou et al., "Alkali-Metal- and Alkaline-Earth-Promoted Catalysts for Coal Liquefaction Applications", Energy & Fuels, vol. 4, No. 1, pp. 38-42 (1990).

Plain et al., "Options for Resid Conversion", Axens IFP Group Technologies, pp. 1-10.

Santori et al., "Eni Slurry Technology: A Technology to Convert the Bottom of the Barrel to Transportation Fuels", 3rd Bottom of the Barrell Technology Conference & Exhibition (Oct. 2004).

Seader et al, "Perry's Chemical Engineers' Handbook", 7th Edition, Section 13—Distillation, 1997, 13-25.

Shen et al., Hydrocracking of Liaohe Vacuum Residue With Bimeta:, Preprints of Symposia—American Chemical society, Division of Fuel Chemistry (1998), 43(3), 481-485, OCDEN: Psadfz, 1998, XP009117504.

Rana et al., A Review of recent advances on process technologies for upgrading of heavy oils and residua, Sep. 7, 2016, full text, retrieved from http://www.sciencedirect.com/science/article/pii/S001623610600295X on Aug. 8, 2017.

Course: Chemical Technology (Organic) Module VI, Lecture 5 Catalytic Cracking: Fluid Catalytic Cracking and Hydrocracking downloaded Jun. 2019.

U.S. Appl. No. 11/117,262, Feb. 4, 2008, Office Action.
U.S. Appl. No. 11/117,202, Apr. 29, 2008, Office Action.
U.S. Appl. No. 11/117,203, Jul. 10, 2008, Office Action.
U.S. Appl. No. 11/117,262, Jul. 17, 2008, Office Action.
U.S. Appl. No. 11/117,202, Aug. 18, 2008, Notice of Allowance.
U.S. Appl. No. 11/117,262, Dec. 5, 2008, Office Action.
U.S. Appl. No. 11/117,203, Dec. 10, 2008, Notice of Allowance.
U.S. Appl. No. 11/117,262, Apr. 30, 2009, Notice of Allowance.
U.S. Appl. No. 11/374,369, May 28, 2009, Office Action.
U.S. Appl. No. 11/117,262, Jun. 26, 2009, Notice of Allowance.

(56) References Cited

OTHER PUBLICATIONS

U.S. Appl. No. 11/932,201, Nov. 23, 2009, Office Action.
U.S. Appl. No. 12/106,112, Jan. 26, 2010, Office Action.
U.S. Appl. No. 11/374,369, Mar. 18, 2010, Office Action.
U.S. Appl. No. 11/932,201, May 13, 2010, Office Action.
U.S. Appl. No. 12/106,112, Jun. 22, 2010, Notice of Allowance.
U.S. Appl. No. 11/968,934, Sep. 20, 2010, Office Action.
U.S. Appl. No. 12/838,761, Nov. 26, 2010, Office Action.
U.S. Appl. No. 11/968,934, Jan. 25, 2011, Office Action.
U.S. Appl. No. 11/932,201, Apr. 21, 2011, Notice of Allowance.
U.S. Appl. No. 12/838,761, May 18, 2011, Office Action.
U.S. Appl. No. 11/932,201, Jun. 8, 2011, Supp Notice of Allowance.
U.S. Appl. No. 11/968,934, Jul. 13, 2011, Final Office Action.
U.S. Appl. No. 12/547,278, Dec. 29, 2011, Office Action.
U.S. Appl. No. 11/968,934, Jan. 6, 2012, Notice of Allowance.
U.S. Appl. No. 13/116,195, Jan. 12, 2012, Office Action.
U.S. Appl. No. 13/116,195, Jul. 11, 2012, Notice of Allowance.
U.S. Appl. No. 13/236,209, Jul. 11, 2012, Notice of Allowance.
U.S. Appl. No. 12/838,761, Jul. 20, 2012, Office Action.
U.S. Appl. No. 13/113,722, Aug. 8, 2012, Office Action.
U.S. Appl. No. 12/547,278, Sep. 7, 2012, Office Action.
U.S. Appl. No. 12/838,761, Jan. 10, 2013, Notice of Allowance.
U.S. Appl. No. 13/113,722, Jan. 22, 2013, Notice of Allowance.
U.S. Appl. No. 13/675,629, Feb. 7, 2013, Office Action.
U.S. Appl. No. 13/675,629, Jun. 14, 2013, Notice of Allowance.
U.S. Appl. No. 13/866,220, Jun. 28, 2013, Office Action.
U.S. Appl. No. 13/866,220, Nov. 6, 2013, Notice of Allowance.
U.S. Appl. No. 11/374,369, Mar. 12, 2014, Office Action.
U.S. Appl. No. 12/547,278, Apr. 22, 2014, Office Action.
U.S. Appl. No. 13/242,979, Aug. 21, 2014, Office Action.
U.S. Appl. No. 11/374,369, Aug. 28, 2014, Office Action.
U.S. Appl. No. 12/547,278, Nov. 24, 2014, Final Office Action.
U.S. Appl. No. 13/242,979, Mar. 12, 2015, Final Office Action.
U.S. Appl. No. 13/865,726, May 12, 2015, Office Action.
U.S. Appl. No. 13/561,479, Aug. 11, 2015, Office Action.
U.S. Appl. No. 13/561,479, Nov. 4, 2015, Final Office Action.
U.S. Appl. No. 13/865,726, Jan. 11, 2016, Final Office Action.
U.S. Appl. No. 13/561,479, Apr. 27, 2016, Office Action.
U.S. Appl. No. 11/374,369, May 18, 2016, Office Action.
U.S. Appl. No. 14/095,698, Jul. 8, 2016, Office Action.
U.S. Appl. No. 13/865,726, Aug. 30, 2016, Office Action.
U.S. Appl. No. 13/561,479, Oct. 21, 2016, Final Office Action.
U.S. Appl. No. 12/547,278, Oct. 28, 2016, Office Action.
U.S. Appl. No. 11/374,369, Nov. 9, 2016, Final Office Action.
U.S. Appl. No. 13/865,726, Jan. 13, 2017, Final Office Action.
U.S. Appl. No. 14/836,792, Apr. 11, 2017, Office Action.
U.S. Appl. No. 12/547,278, Apr. 14, 2017, Final Office Action.
U.S. Appl. No. 13/865,726, Apr. 26, 2017, Office Action.
U.S. Appl. No. 13/865,726, Aug. 14, 2017, Final Office Action.
U.S. Appl. No. 11/374,369, Sep. 1, 2017, Office Action.
U.S. Appl. No. 14/836,792, Sep. 25, 2017, Final Office Action.
U.S. Appl. No. 12/547,278, Nov. 29, 2017, Office Action.
U.S. Appl. No. 15/258,653, Apr. 2, 2018, Office Action.
U.S. Appl. No. 15/258,706, Apr. 2, 2018, Office Action.
U.S. Appl. No. 15/615,574, Apr. 2, 2018, Office Action.
U.S. Appl. No. 11/374,369, Apr. 24, 2018, final Office Action.
U.S. Appl. No. 15/354,230, Jun. 12, 2018, Office Action.
U.S. Appl. No. 15/258,653, Sep. 21, 2018, Final Office Action.
U.S. Appl. No. 15/258,653, Mar. 8, 2019, Office Action.
U.S. Appl. No. 15/258,653, Jul. 18, 2019, Final Office Action.
U.S. Appl. No. 15/258,706, Sep. 21, 2018, Final Office Action.
U.S. Appl. No. 15/258,706, Mar. 8, 2019, Office Action.
U.S. Appl. No. 15/258,706, Jul. 23, 2019, Final Office Action.
U.S. Appl. No. 15/615,574, Sep. 21, 2018, Final Office Action.
U.S. Appl. No. 15/615,574, Mar. 21, 2019, Office Action.
U.S. Appl. No. 15/615,574, Jul. 25, 2019, Final.
U.S. Appl. No. 15/098,111, Sep. 9, 2019, Office Action.
Kressmann et al., "Improvements of Ebullated-Bed Technology for Upgrading Heavy", Oil & Gas Science and Technology, vol. 55, No. 4, 2000, pp. 397-406.
Rana et al., "A review of recent advances on process technologies for upgrading of heavy oils and residua", Fuel, vol. 86, (2007), pp. 1216-1231.
Ex Parte Quayle Action received for U.S. Appl. No. 11/374,369, dated Sep. 21, 2020, 5 pages.
Hydrocracking of Liaohe Vacuum Residue With Bimeta:, Shen et al., Preprints of Symposia—American Chemical society, Division of Fuel Chemistry (1998), 43(3), 481-485, OCDEN: Psadfz, 1998,XP009117504.
Lee, Sunggyu et al, Handook of Alternative Fuel Technologies, 2007, pp. 187-188.
Lewis, Richard J., Hawley's Condensed Chemical Dictionary, 15 Edition, 2007, p. 321.
N. Panariti et al.: "petroleum Residue Upgrading with Dispered Catalysts Part 1. Catalysts Activity and Selctivity" Applied Catalysts A: General, vol. 204, Mar. 31, 2000 (Mar. 1, 2000) pp. 203-213.
Notice of Allowance dated Aug. 5, 2010 cited in U.S. Appl. No. 11/461,652.
Notice of Allowance dated Oct. 27, 2009 cited in U.S. Appl. No. 11/327,085.
Office Action dated Apr. 2, 2009 cited in U.S. Appl. No. 11/327,085.
Office Action dated Mar. 8, 2010 cited in U.S. Appl. No. 11/461,652.
Office Action dated Sep. 16, 2010 cited in U.S. Appl. No. 11/968,861.
Office Action dated Sep. 30, 2009 cited in U.S. Appl. No. 11/461,652.
Office Action received for EA Patent Application No. 201892721, dated Jul. 8, 2020, 8 pages ( 4 pages of English Translation and 4 pages of Original Document).
Office Action received for U.S. Appl. No. 13/236,209 dated Feb. 21, 2012.
U.S. Appl. filed Apr. 18, 2013, Lott et al., U.S. Appl. No. 13/856,726.
U.S. Appl. filed Dec. 3, 2013, Lott et al., U.S. Appl. No. 14/095,698.
U.S. Appl. No. 11/327,249, filed Jan. 6, 2006, Zhou et al.
U.S. Appl. No. 11/968,861, filed Feb. 2, 2011, Notice of Allowance.
U.S. Application Filed on Apr. 19, 2013, by Lott et al., U.S. Appl. No. 13/866,220.
U.S. Application Filed on Nov. 17, 2015, by Lott et al., U.S. Appl. No. 15/354,230.
U.S. Application Filed on Sep. 7, 2016, by Mountainland et al., U.S. Appl. No. 15/258,653.
U.S. Application Filed on Sep. 7, 2016, by Mountainland et al., U.S. Appl. No. 15/258,706.
U.S. Patent Application filed on Apr. 19, 2013, by Lott et al., U.S. Appl. No. 13/865,726.
U.S. Patent Application filed on May 23, 2011, by Lott et al., U.S. Appl. No. 13/113,722.
U.S. Appl. filed May 26, 2011, Lott et al., U.S. Appl. No. 13/116,195.

UPGRADED EBULLATED BED REACTOR WITH NO RECYCLE BUILDUP OF ASPHALTENES IN VACUUM BOTTOMS

CROSS REFERENCE TO RELATED APPLICATION

This Application claims the benefit of U.S. Provisional Application No. 62/746,867, filed Oct. 17, 2018, which is incorporated herein by reference in its entirety.

BACKGROUND OF THE INVENTION

1. The Field of the Invention

The invention relates to heavy oil hydroprocessing methods and systems, including ebullated bed hydroprocessing methods and systems which utilize a dual catalyst system with recycling of vacuum bottoms and no recycle buildup of asphaltenes.

2. The Relevant Technology

Converting heavy oil into useful end products involves extensive processing, such as reducing the boiling point of the heavy oil, increasing the hydrogen-to-carbon ratio, and removing impurities such as metals, sulfur, nitrogen, and coke precursors. Examples of hydrocracking processes using conventional heterogeneous catalysts to upgrade atmospheric tower bottoms include fixed-bed hydroprocessing, ebullated-bed hydroprocessing, and moving-bed hydroprocessing. Noncatalytic upgrading processes for upgrading vacuum tower bottoms include thermal cracking, such as delayed coking, flexicoking, visbreaking, and solvent extraction.

There is an ever-increasing demand to more efficiently utilize low quality heavy oil feedstocks and extract fuel values therefrom. Low quality feedstocks are characterized as including relatively high quantities of hydrocarbons that nominally boil at or above 524° C. (975° F.). They also contain relatively high concentrations of sulfur, nitrogen and/or metals. High boiling fractions derived from these low quality feedstocks typically have a high molecular weight (often indicated by higher density and viscosity) and/or low hydrogen/carbon ratio, which is related to the presence of high concentrations of undesirable components, including asphaltenes and carbon residue. Asphaltenes and carbon residue are difficult to process and commonly cause fouling of conventional catalysts and hydroprocessing equipment because they contribute to the formation of coke and sediment.

Lower quality heavy oil feedstocks contain higher concentrations of asphaltenes, carbon residue, sulfur, nitrogen, and metals. Examples include heavy crude, oil sands bitumen, and residuum left over from conventional refinery process. Residuum (or "resid") can refer to atmospheric tower bottoms and vacuum tower bottoms. Atmospheric tower bottoms can have a boiling point of at least 343° C. (650° F.) although it is understood that the cut point can vary among refineries and be as high as 380° C. (716° F.). Vacuum tower bottoms (also known as "resid pitch" or "vacuum residue") can have a boiling point of at least 524° C. (975° F.), although it is understood that the cut point can vary among refineries and be as high as 538° C. (1000° F.) or even 565° C. (1050° F.).

By way of comparison, Alberta light crude contains about 9% by volume vacuum residue, while Lloydminster heavy oil contains about 41% by volume vacuum residue, Cold Lake bitumen contains about 50% by volume vacuum residue, and Athabasca bitumen contains about 51% by volume vacuum residue. As a further comparison, a relatively light oil such as Dansk Blend from the North Sea region only contains about 15% vacuum residue, while a lower-quality European oil such as Ural contains more than 30% vacuum residue, and an oil such as Arab Medium is even higher, with about 40% vacuum residue.

In a given ebullated bed system, the rate of production of converted products is often limited by fouling. When attempts are made to increase production of converted products beyond a certain practical limit, the rate of fouling of certain heat exchangers or other process equipment becomes too rapid, requiring more frequent shutdowns for maintenance and cleaning. One way to increase production of converted products is to recycle vacuum bottoms produced during vacuum distillation of upgraded hydrocarbons produced by the ebullated bed reactor. However, this typically causes recycle buildup of asphaltenes in the vacuum bottoms, limiting the ability to maintain a desired conversion without sediment buildup and equipment fouling. It also yields lower quality vacuum bottom products, which can be used as fuel oil.

Typically, a refinery relates the observed rate of equipment fouling to measurements of sediment production and arrives at an operating sediment limit, above which the refinery will avoid operating the ebullated bed hydrocracker. Furthermore, sediment production and equipment fouling place limitations on downstream processing of high boiling fractions. They also limit or prevent recycling of vacuum bottoms to the hydroprocessing reactor. Such problems are exacerbated when using lower quality heavy oil feedstocks. Even when a refinery finds a way to recycle vacuum bottoms, the result can be a final bottoms product that is of low quality and fails to meet minimum standards for use as fuel oil. There remains a need to find ways to recycle vacuum bottoms without causing recycle buildup of asphaltenes, which increases the risk of equipment fouling and shutdown and produces lower quality bottoms product.

SUMMARY OF THE INVENTION

Disclosed herein are methods for upgrading an ebullated bed hydroprocessing system to permit recycling of vacuum bottoms without recycle buildup of asphaltenes. Also disclosed are upgraded ebullated bed hydroprocessing systems that utilize recycled vacuum bottoms without recycle buildup of asphaltenes. The disclosed methods and systems involve the use of a dual catalyst system comprised of a solid supported catalyst and well-dispersed (e.g., homogeneous) catalyst particles. The dual catalyst system permits operating an ebullated bed reactor with recycling of vacuum bottoms without recycle buildup of asphaltenes in the ebullated bed hydroprocessing system.

In some embodiments, a method of upgrading an ebullated bed hydroprocessing system to permit recycling of vacuum bottoms without recycle buildup of asphaltenes comprises: (1) operating an ebullated bed reactor using a heterogeneous catalyst to hydroprocess heavy oil at baseline conditions, optionally with recycling of vacuum bottoms and recycle buildup of asphaltenes; (2) adding or forming in situ dispersed metal sulfide catalyst particles in the ebullated bed reactor to yield upgraded ebullated bed reactor with a dual catalyst system comprised of the heterogeneous catalyst and dispersed metal sulfide catalyst particles; (3) operating the upgraded ebullated bed reactor using the dual catalyst system to hydroprocess heavy oil to produce hydrocarbon products; (4) subjecting the hydrocarbon products to vacuum distillation and separating distillates from vacuum bottoms containing residual metal sulfide catalyst particles; and (5) recycling at least a portion of the vacuum bottoms containing residual metal sulfide catalyst particles into the upgraded ebullated bed reactor without recycle buildup of asphaltenes in the ebullated bed hydroprocessing system.

In some embodiments, operating the upgraded ebullated bed reactor using the dual catalyst system with recycling of vacuum bottoms includes: (i) operating the upgraded ebullated bed reactor at higher conversion compared to the baseline conditions without recycle buildup of asphaltenes in the ebullated bed hydroprocessing system; (ii) operating the upgraded ebullated bed reactor at similar conversion compared to the baseline conditions with reduced asphaltenes in the vacuum bottoms; or (iii) operating the upgraded ebullated bed reactor at higher conversion compared to the baseline conditions with reduced asphaltenes in the vacuum bottoms. The third scenario can include any combination of increased conversion and reduced asphaltenes in bottoms product and may depend on the quality of the feedstock (e.g., sediment forming tendency), which can be variable, the rate of equipment fouling, and/or the desired quality of bottoms products to be used as fuel oil or other end product.

In some embodiments, the vacuum bottoms can be recycled at a recycle ratio of from about 1% to about 50%, preferably from about 5% to about 40%, and more preferably from about 10% to about 30%. The recycle ratio can be expressed as a percentage determined by the ratio of vacuum bottoms recycle amount to the fresh feedstock amount, either on a volumetric or mass basis. These percentages indicate the flow rate of the vacuum bottoms as a volume percent of the fresh feedstock flow rate. The recycle ratio may also be readily converted to a mass percent basis, if the densities of the feedstock and vacuum bottoms are known.

In some embodiments, recycling of vacuum bottoms without recycle buildup of asphaltenes in the vacuum bottoms results in increased rate of production of converted products compared to baseline conditions. In some embodiments, throughput can be increased by at least 2.5%, at least 5%, at least 10%, or at least 20% compared to baseline conditions. In some embodiments, conversion can be increased by at least 2.5%, at least 5%, at least 7.5%, at least 10%, or at least 15% compared to baseline conditions. In some embodiments, the operating temperature of the upgraded ebullated bed reactor can be increased by at least 2.5° C., at least 5° C., at least 7.5° C., or at least 10° C. compared to baseline conditions.

In some embodiments, the rate of equipment fouling can be the same or less when operating the upgraded ebullated bed reactor with recycling of vacuum bottoms compared to baseline conditions. In some embodiments, operating the ebullated bed reactor with recycling of vacuum bottoms can decrease the rate of equipment fouling by at least 5%, at least 25%, at least 50%, or at least 75% compared to equipment fouling at baseline conditions.

The rate of equipment fouling can be measured by at least one of: (i) frequency of required heat exchanger clean-outs; (ii) frequency of switching to spare heat exchangers; (iii) frequency of filter changes; (iv) frequency of strainer clean-outs or changes; (v) rate of decrease in equipment skin temperatures, including in equipment selected from heat exchangers, separators, or distillation towers; (vi) rate of increase in furnace tube metal temperatures; (vii) rate of increase in calculated fouling resistance factors for heat exchangers and furnaces; (viii) rate of increase in differential pressure of heat exchangers; (ix) frequency of cleaning atmospheric and/or vacuum distillation towers; or (x) frequency of maintenance turnarounds.

In some embodiments, the dispersed metal sulfide catalyst particles are less than 1 μm in size, or less than about 500 nm in size, or less than about 250 nm in size, or less than about 100 nm in size, or less than about 50 nm in size, or less than about 25 nm in size, or less than about 10 nm in size, or less than about 5 nm in size.

In some embodiments, the dispersed metal sulfide catalyst particles can be formed in situ within the heavy oil from a catalyst precursor. By way of example and not limitation, the dispersed metal sulfide catalyst particles can be formed by blending a catalyst precursor into an entirety of the heavy oil prior to thermal decomposition of the catalyst precursor and formation of active metal sulfide catalyst particles. By way of further example, methods may include mixing a catalyst precursor with a diluent hydrocarbon to first form a diluted precursor mixture, followed by blending the diluted precursor mixture with the heavy oil to form conditioned heavy oil, and heating the conditioned heavy oil to decompose the catalyst precursor and form the dispersed metal sulfide catalyst particles in situ within the heavy oil.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which.

DETAILED DESCRIPTION OF THE PREFERRED EMBODIMENTS

I. Introduction and Definitions

The present invention relates to methods for upgrading an ebullated bed hydroprocessing system to permit recycling vacuum bottoms without recycle buildup of asphaltenes (e.g., in the hydroprocessing system, such the ebullated bed reactor and/or vacuum bottoms). An upgraded ebullated bed system is created by carrying out the disclosed method.

The terms "asphaltene" and "asphaltenes" shall refer to materials in a heavy oil feedstock that are typically insoluble in paraffinic solvents such as propane, butane, pentane, hexane, and heptane. Asphaltenes can include sheets of condensed ring compounds held together by heteroatoms such as sulfur, nitrogen, oxygen and metals. Asphaltenes broadly include a wide range of complex compounds having anywhere from 80 to 1200 carbon atoms, with predominating molecular weights, as determined by solution techniques, in the 1200 to 16,900 range. About 80-90% of the metals in the crude oil are contained in the asphaltene fraction which, together with a higher concentration of non-metallic heteroatoms, renders the asphaltene molecules more hydrophilic and less hydrophobic than other hydrocarbons in crude.

Figure 1:
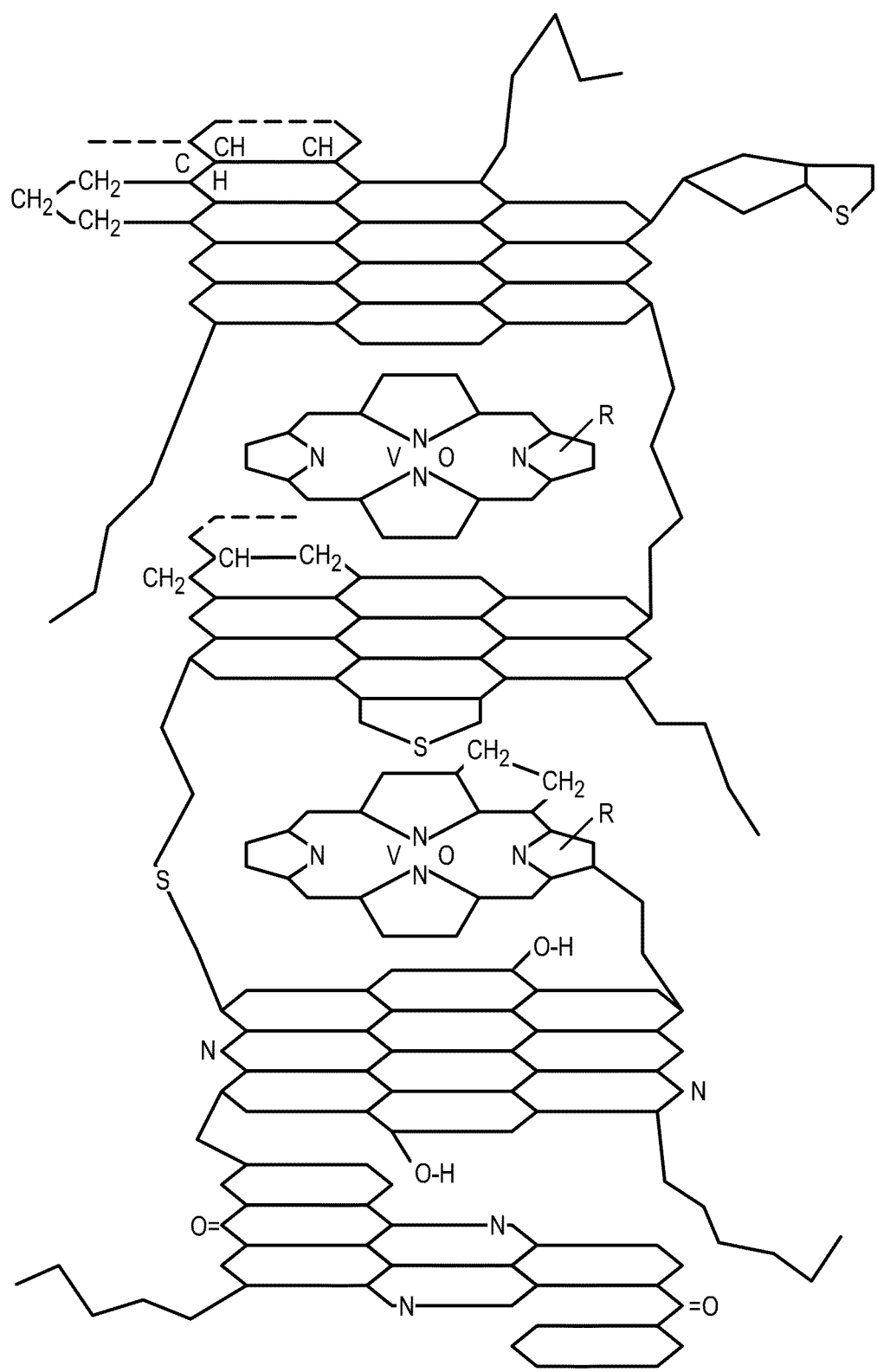
FIG. 1 depicts a hypothetical molecular structure of asphaltene.

A hypothetical asphaltene molecule structure developed by A.G. Bridge and co-workers at Chevron is depicted in FIG. 1. Generally, asphaltenes are typically defined based on the results of insolubles methods, and more than one definition of asphaltenes may be used. Specifically, a commonly used definition of asphaltenes is heptane insolubles minus toluene insolubles (i.e., asphaltenes are soluble in toluene; sediments and residues insoluble in toluene are not counted as asphaltenes). Asphaltenes defined in this fashion may be referred to as "$C_7$ asphaltenes". However, an alternate definition may also be used with equal validity, measured as pentane insolubles minus toluene insolubles, and commonly referred to as "$C_5$ asphaltenes". In the examples of the present invention, the $C_7$ asphaltene definition is used, but the $C_5$ asphaltene definition can be readily substituted.

The term "recycle buildup of asphaltenes" refers to situations where recycling of vacuum bottoms back into the ebullated bed reactor results in a higher concentration of asphaltenes in the ebullated bed hydroprocessing system, such as the ebullated bed reactor and/or vacuum bottoms. For example, at any given reactor conditions, such as conversion, temperature and/or throughput, recycle buildup of asphaltenes when recycling vacuum bottoms means that the asphaltene concentration increases even when conversion remains constant due to the increased concentration of asphaltenes in the vacuum bottoms compared to the heavy oil feedstsock. In such cases, the ebullated bed reactor is unable to effectively hydroprocess and convert the additional asphaltenes at a high enough rate to prevent recycle buildup of asphaltenes. This results in increased sediment buildup and equipment fouling, more frequent shutdowns for cleaning, and vacuum bottoms of lower quality. Recycle buildup of asphaltenes can refer to an increased steady-state concentration of asphaltenes.

Operating an upgraded ebullated bed reactor with recycling of vacuum bottoms "without recycle building of asphaltenes" means that the asphaltene content in the ebullated bed hydroprocessing system, including the ebullated bed reactor, remains at the same or lower level than would have occurred in the absence of recycling. In some cases, asphaltene concentration may even drop when operating at the same conversion compared to baseline conditions, or even at higher conversion, when recycling vacuum bottoms into an upgraded ebullated bed reactor using a dual catalyst system. This is unexpected because increased conversion typically results in higher sediment formation and equipment fouling, all things being equal.

The term "sediment" refers to solids formed in a liquid stream that can settle out. Sediments can include inorganics, coke, or insoluble asphaltenes that precipitate after conversion. Sediment in petroleum products is commonly measured using the IP-375 hot filtration test procedure for total sediment in residual fuel oils published as part of ISO 10307 and ASTM D4870. Other tests include the IP-390 sediment test and the Shell hot filtration test. Sediment is related to components of the oil that have a propensity for forming solids during processing and handling. These solid-forming components have multiple undesirable effects in a hydroconversion process, including degradation of product quality (e.g., vacuum bottoms quality) and operability problems related to equipment fouling. It should be noted that although the strict definition of sediment is based on the measurement of solids in a sediment test, it is common for the term to be used more loosely to refer to the solids-forming components of the oil itself, which may not be present in the oil as actual solids, but which contribute to solids formation under certain conditions.

All crudes have a vacuum resid component that has a characteristic "sediment forming tendency". Although the sediment forming tendency of a heavy oil feedstock is not always quantifiable, some heavy oil feedstocks have lesser or greater sediment forming tendencies, For example, Eastern European crude oils such as Ural, South American crude oils such as Venezuelan and Colombian, and some Central or North American crude oils such as Mexican, and certain Gulf of Mexico crudes have vacuum resid components that have significantly higher sediment forming tendency compared to ordinary crudes, such as West Texas Intermediate crude oil, Alaska North Slope crude oil, many African crude oils, North Sea crude oils, and most Middle Eastern crude oils, including Arabian Medium Crude, Arabian Heavy Crude, and Bonny Light Crude.

The term "fouling" refers to the formation of an undesirable phase (foulant) that interferes with processing. The foulant is normally a carbonaceous material or solid that deposits and collects within the processing equipment. Equipment fouling can result in loss of production due to equipment shutdown, decreased performance of equipment, increased energy consumption due to the insulating effect of foulant deposits in heat exchangers or heaters, increased maintenance costs for equipment cleaning, reduced efficiency of fractionators, and reduced reactivity of heterogeneous catalyst.

The "rate of equipment fouling" before and after upgrading a hydrocracking reactor to use the dual catalyst system can be determined by at least one of: (i) frequency of required heat exchanger clean-outs; (ii) frequency of switching to spare heat exchangers; (iii) frequency of filter changes; (iv) frequency of strainer clean-outs or changes; (v) rate of decrease in equipment skin temperatures, including in equipment selected from heat exchangers, separators, or distillation towers; (vi) rate of increase in furnace tube metal temperatures; (vii) rate of increase in calculated fouling resistance factors for heat exchangers and furnaces; (viii) rate of increase in differential pressure of heat exchangers; (ix) frequency of cleaning atmospheric and/or vacuum distillation towers; or (x) frequency of maintenance turnarounds.

The term "heavy oil feedstock" refers to heavy crude, oil sands bitumen, bottom of the barrel and residuum left over from refinery processes (e.g., visbreaker bottoms), and any other lower quality materials that contain a substantial quantity of high boiling hydrocarbon fractions and/or that include a significant quantity of asphaltenes that can deactivate a heterogeneous catalyst and/or cause or result in the formation of coke precursors and sediment. Examples of heavy oil feedstocks include, but are not limited to, Lloydminster heavy oil, Cold Lake bitumen, Athabasca bitumen, atmospheric tower bottoms, vacuum tower bottoms, residuum (or "resid"), resid pitch, vacuum residue (e.g., Ural VR, Arab Medium VR, Athabasca VR, Cold Lake VR, Maya VR, and Chichimene VR), deasphalted liquids obtained by solvent deasphalting, asphaltene liquids obtained as a byproduct of deasphalting, and nonvolatile liquid fractions that remain after subjecting crude oil, bitumen from tar sands, liquefied coal, oil shale, or coal tar feedstocks to distillation, hot separation, solvent extraction, and the like. By way of further example, atmospheric tower bottoms (ATB) can have a nominal boiling point of at least 343° C. (650° F.) although it is understood that the cut point can vary among refineries and be as high as 380° C. (716° F.). Vacuum tower bottoms can have a nominal boiling point of at least 524° C. (975° F.), although it is understood that the cut point can vary among refineries and be as high as 538° C. (1000° F.) or even 565° C. (1050° F.).

The "quality" of heavy oil can be measured by at least one characteristic selected from, but not limited to: (i) boiling point; (ii) concentration of sulfur; (iii) concentration of nitrogen; (iv) concentration of metals; (v) molecular weight; (vi) hydrogen to carbon ratio; (vii) asphaltene content; and (viii) sediment forming tendency.

A "lower quality heavy oil" and/or "lower quality feedstock blend" can have at least one lower quality characteristic compared to an initial heavy oil feedstock selected from, but not limited to: (i) higher boiling point; (ii) higher concentration of sulfur; (iii) higher concentration of nitrogen; (iv) higher concentration of metals; (v) higher molecular weight (often indicated by higher density and viscosity); (vi) lower hydrogen to carbon ratio; (vii) higher asphaltene content; and (viii) greater sediment forming tendency.

The term "opportunity feedstock" refers to lower quality heavy oils and lower quality heavy oil feedstock blends having at least one lower quality characteristic compared to an initial heavy oil feedstock. An opportunity feedstock also typically has a lower market value (or price) compared to an initial feedstock.

The terms "hydrocracking" and "hydroconversion" shall refer to a process whose primary purpose is to reduce the boiling range of a heavy oil feedstock and in which a substantial portion of the feedstock is converted into products with boiling ranges lower than that of the original feedstock. Hydrocracking or hydroconversion generally involves fragmentation of larger hydrocarbon molecules into smaller molecular fragments having a fewer number of carbon atoms and a higher hydrogen-to-carbon ratio. The mechanism by which hydrocracking occurs typically involves the formation of hydrocarbon free radicals during thermal fragmentation, followed by capping of the free radical ends or moieties with hydrogen. The hydrogen atoms or radicals that react with hydrocarbon free radicals during hydrocracking can be generated at or by active catalyst sites.

The term "hydrotreating" shall refer to operations whose primary purpose is to remove impurities such as sulfur, nitrogen, oxygen, halides, and trace metals from the feedstock and saturate olefins and/or stabilize hydrocarbon free radicals by reacting them with hydrogen rather than allowing them to react with themselves. The primary purpose is not to change the boiling range of the feedstock. Hydrotreating is most often carried out using a fixed bed reactor, although other hydroprocessing reactors can also be used for hydrotreating, an example of which is an ebullated bed hydrotreater.

Of course, "hydrocracking" or "hydroconversion" may also involve the removal of sulfur and nitrogen from a feedstock as well as olefin saturation and other reactions typically associated with "hydrotreating". The terms "hydroprocessing" and "hydroconversion" shall broadly refer to both "hydrocracking" and "hydrotreating" processes, which define opposite ends of a spectrum, and everything in between along the spectrum.

The term "hydrocracking reactor" shall refer to any vessel in which hydrocracking (i.e., reducing the boiling range) of a feedstock in the presence of hydrogen and a hydrocracking catalyst is the primary purpose. Hydrocracking reactors are characterized as having an inlet port into which a heavy oil feedstock and hydrogen can be introduced, an outlet port from which an upgraded feedstock or material can be withdrawn, and sufficient thermal energy so as to form hydrocarbon free radicals in order to cause fragmentation of larger hydrocarbon molecules into smaller molecules. Examples of hydrocracking reactors include, but are not limited to, slurry phase reactors (i.e., a two phase, gas-liquid system), ebullated bed reactors (i.e., a three phase, gas-liquid-solid system), fixed bed reactors (i.e., a three-phase system that includes a liquid feed trickling downward over or flowing upward through a fixed bed of solid heterogeneous catalyst with hydrogen typically flowing cocurrently, but possibly countercurrently, to the heavy oil).

The term "hydrocracking temperature" shall refer to a minimum temperature required to cause significant hydrocracking of a heavy oil feedstock. In general, hydrocracking temperatures will preferably fall within a range of about 399° C. (750° F.) to about 460° C. (860° F.), more preferably in a range of about 418° C. (785° F.) to about 443° C. (830° F.), and most preferably in a range of about 421° C. (790° F.) to about 440° C. (825° F.).

The term "gas-liquid slurry phase hydrocracking reactor" shall refer to a hydroprocessing reactor that includes a continuous liquid phase and a gaseous dispersed phase, which forms a "slurry" of gaseous bubbles within the liquid phase. The liquid phase typically comprises a hydrocarbon feedstock that may contain a low concentration of dispersed metal sulfide catalyst particles, and the gaseous phase typically comprises hydrogen gas, hydrogen sulfide, and vaporized low boiling point hydrocarbon products. The liquid phase can optionally include a hydrogen donor solvent. The term "gas-liquid-solid, 3-phase slurry hydrocracking reactor" is used when a solid catalyst is employed along with liquid and gas. The gas may contain hydrogen, hydrogen sulfide and vaporized low boiling hydrocarbon products. The term "slurry phase reactor" shall broadly refer to both type of reactors (e.g., those with dispersed metal sulfide catalyst particles, those with a micron-sized or larger particulate catalyst, and those that include both).

The terms "solid heterogeneous catalyst", "heterogeneous catalyst" and "supported catalyst" shall refer to catalysts typically used in ebullated bed and fixed bed hydroprocessing systems, including catalysts designed primarily for hydrocracking, hydroconversion, hydrodemetallization, and/or hydrotreating. A heterogeneous catalyst typically comprises: (i) a catalyst support having a large surface area and interconnected channels or pores; and (ii) fine active catalyst particles, such as sulfides of cobalt, nickel, tungsten, and molybdenum dispersed within the channels or pores. The pores of the support are typically of limited size to maintain mechanical integrity of the heterogeneous catalyst and prevent breakdown and formation of excessive fines in the reactor. Heterogeneous catalysts can be produced as cylindrical pellets, cylindrical extrudates, other shapes such as trilobes, rings, saddles, or the like, or spherical solids.

The terms "dispersed metal sulfide catalyst particles" and "dispersed catalyst" shall refer to catalyst particles having a particle size that is less than 1 μm (submicron, or sub micrometer), e.g., less than about 500 nm in diameter, or less than about 250 nm in diameter, or less than about 100 nm in diameter, or less than about 50 nm in diameter, or less than about 25 nm in diameter, or less than about 10 nm in diameter, or less than about 5 nm in diameter. The term "dispersed metal sulfide catalyst particles" may include molecular or molecularly-dispersed catalyst compounds. The term "dispersed metal sulfide catalyst particles" typically excludes metal sulfide particles and agglomerates of metal sulfide particles that are larger than 1 μm.

The term "molecularly-dispersed catalyst" shall refer to catalyst compounds that are essentially "dissolved" or dissociated from other catalyst compounds or molecules in a hydrocarbon feedstock or suitable diluent. It can include very small catalyst particles that contain a few catalyst molecules joined together (e.g., 15 molecules or less).

The terms "residual catalyst particles" and "residual dispersed metal sulfide catalyst particles" shall refer to catalyst particles that remain with a hydrocarbon product when transferred from one vessel to another (e.g., from a hydroprocessing reactor to a separator and/or other hydroprocessing reactor). Residual dispersed metal sulfide catalyst particles may also remain in the liquid residual fraction after separation of a hydrocarbon product into distillates and residual liquid, such as by hot separation, atmospheric distillation, or vacuum distillation.

The term "conditioned feedstock" shall refer to a hydrocarbon feedstock into which a catalyst precursor has been combined and mixed sufficiently so that, upon decomposition of the catalyst precursor and formation of the active catalyst, the catalyst will comprise dispersed metal sulfide catalyst particles formed in situ within the feedstock.

The terms "upgrade", "upgrading" and "upgraded", when used to describe a feedstock that is being or has been subjected to hydroprocessing, or a resulting material or product, shall refer to one or more of a reduction in the molecular weight of the feedstock, a reduction in the boiling point range of the feedstock, a reduction in the concentration of asphaltenes, a reduction in the concentration of hydrocarbon free radicals, and/or a reduction in the quantity of impurities, such as sulfur, nitrogen, oxygen, halides, and metals.

The term "severity" generally refers to the amount of energy that is introduced into heavy oil during hydroprocessing and is often related to the operating temperature of the hydroprocessing reactor (i.e., higher temperature is related to higher severity; lower temperature is related to lower severity) in combination with the duration of said temperature exposure. Increased severity generally increases the quantity of converted products produced by the hydroprocessing reactor, including both desirable products and undesirable products.

Desirable conversion products include hydrocarbons of reduced molecular weight, boiling point, and specific gravity, which can include end products such as naphtha, diesel, jet fuel, kerosene, wax, fuel oil, and the like. Other desirable conversion products include higher boiling hydrocarbons that can be further processed using conventional refining and/or distillation processes. Bottoms product of sufficient quality to be useful as fuel oil is another example of a desirable conversion product Undesirable conversion products include coke, sediment, metals, and other solid materials that can deposit on hydroprocessing equipment and cause fouling, such as interior components of reactors, separators, filters, pipes, towers, heat exchangers, and the heterogeneous catalyst. Undesirable conversion products can also refer to unconverted resid that remains after distillation, such as atmospheric tower bottoms ("ATB") or vacuum tower bottoms ("VTB"), particularly that are of too low of quality to be useful as fuel oil or other desired use. Minimizing undesirable conversion products reduces equipment fouling and shutdowns required to clean the equipment. Nevertheless, there may be a desirable amount of unconverted resid in order for downstream separation equipment to function properly and/or in order to provide a liquid transport medium for containing coke, sediment, metals, and other solid materials that might otherwise deposit on and foul equipment but that can be transported away by the remaining resid.

In addition to temperature, "severity" can be related to one or both of "conversion" and "throughput". Whether increased severity involves increased conversion and/or increased or decreased throughput may depend on the quality of the heavy oil feedstock and/or the mass balance of the overall hydroprocessing system. For example, where it is desired to convert a greater quantity of feed material and/or provide a greater quantity of material to downstream equipment, increased severity may primarily involve increased throughput without necessarily increasing fractional conversion. This can include the case where resid fractions (ATB and/or VTB) are sold as fuel oil and increased conversion without increased throughput might decrease the quantity of this product. In the case where it is desired to increase the ratio of upgraded materials to resid fractions, it may be desirable to primarily increase conversion without necessarily increasing throughput. Where the quality of heavy oil introduced into the hydroprocessing reactor fluctuates, it may be desirable to selectively increase or decrease one or both of conversion and throughput to maintain a desired ratio of upgraded materials to resid fractions and/or a desired absolute quantity or quantities of end product(s) being produced.

The terms "conversion" and "fractional conversion" refer to the proportion, often expressed as a percentage, of heavy oil that is converted into lower boiling and/or lower molecular weight materials. The conversion is expressed as a percentage of the initial resid content (i.e. components with boiling point greater than a defined residue cut point) which is converted to products with boiling point less than the defined cut point. The definition of residue cut point can vary, and can nominally include 524° C. (975° F.), 538° C. (1000° F.), 565° C. (1050° F.), and the like. It can be measured by distillation analysis of feed and product streams to determine the concentration of components with boiling point greater than the defined cut point. Fractional conversion is expressed as (F–P)/F, where F is the quantity of resid in the combined feed streams, and P is the quantity in the combined product streams, where both feed and product resid content are based on the same cut point definition. The quantity of resid is most often defined based on the mass of components with boiling point greater than the defined cut point, but volumetric or molar definitions could also be used.

The conversion of asphaltenes can be different than the conversion of heavy oil feedstock as a whole. For purposes of this disclosure, a useful definition of asphaltene conversion is based on the amount of asphaltenes in the fresh feedstock and can be defined by the following, which results in a decimal fraction between 0 and 1, which can be converted into a percentage by multiplying by 100:

Conv=[Asph(fresh feed)−Asph(products)]/Asph(fresh feed).

The asphaltene content of the recycle stream is internal to the process. When conversion of asphaltenes is too low compared to conversion of heavy oil as a whole, recycle buildup of asphaltenes can occur.

The term "throughput" refers to the quantity of feed material that is introduced into the hydroprocessing reactor as a function of time. Throughput can be expressed in volumetric terms, such as barrels per day, or in mass terms, such as metric tons per hour. In common usage, throughput is defined as the mass or volumetric feed rate of only the heavy oil feedstock itself (for example, vacuum tower bottoms or the like). The definition does not normally include quantities of diluents or other components that may sometimes be included in the overall feeds to a hydroconversion unit, although a definition which includes those other components could also be used.

The "production rate of converted products" is an absolute rate that can be expressed in volumetric terms, such as barrels per day, or in mass terms, such as metric tons per hour. The "production rate of converted products" should not be confused with yield or efficiency, which are sometimes erroneously called "rate" (e.g., production rate per unit feed rate, or production rate per unit converted feed). It will be appreciated that the actual numeric values of both initial production rate of converted products and increased production rate of converted products are specific to an individual production facility and depend on the capacity of that facility. Therefore, it is valid to compare the production rate of the unit or facility in question before and after upgrading but not against a different unit or facility built with a different capacity.

II. Ebullated Bed Hydroprocessing Reactors and Systems

FIGS. 2A-2D schematically depict non-limiting examples of ebullated bed hydroprocessing reactors and systems used to hydroprocess hydrocarbon feedstocks such as heavy oil, which can be upgraded to use a dual catalyst system according to the invention. It will be appreciated that the example ebullated bed hydroprocessing reactors and systems can include interstage separation, integrated hydrotreating, and/or integrated hydrocracking.

Figure 2A:
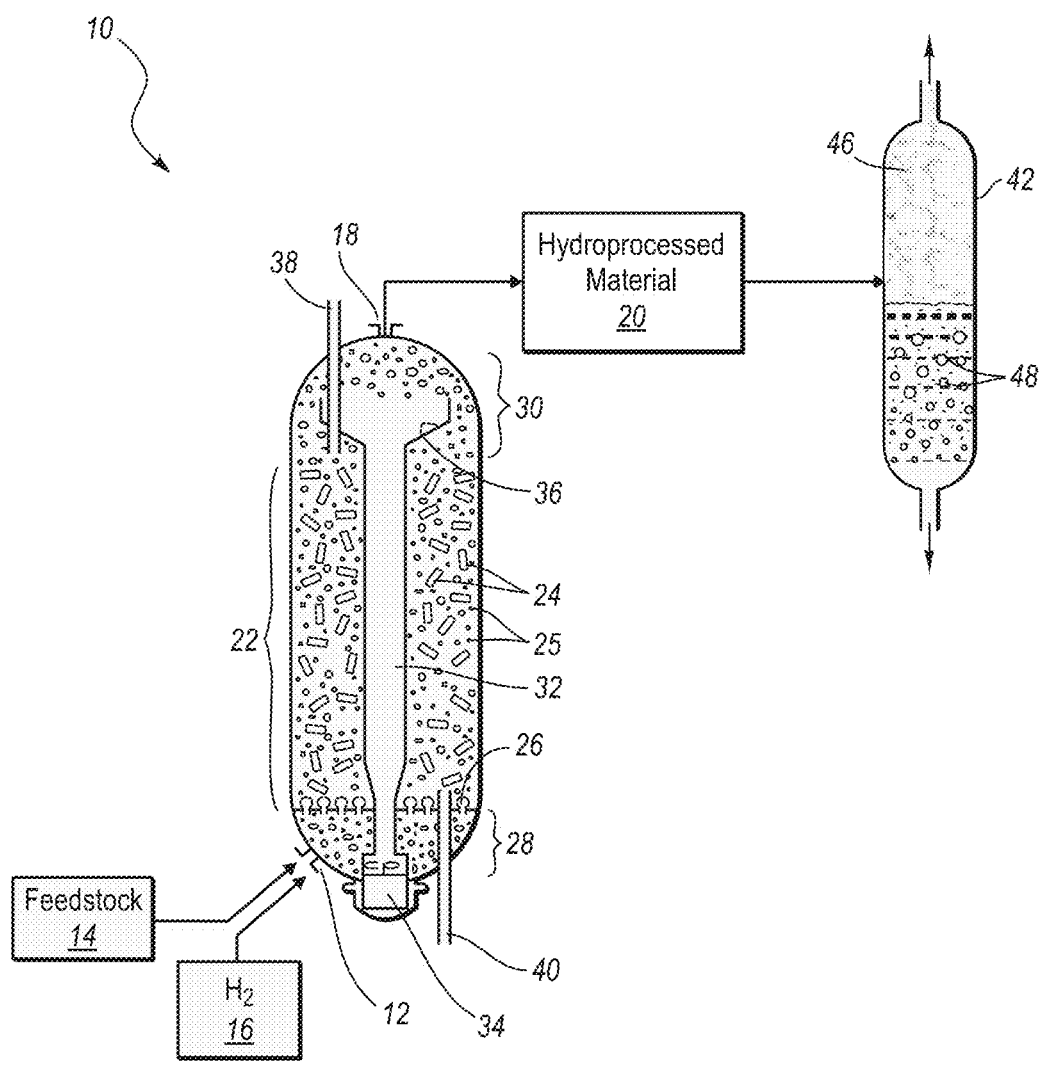
FIGS. 2A and 2B schematically illustrate exemplary ebullated bed reactors.

FIG. 2A schematically illustrates an ebullated bed hydroprocessing reactor 10 used in the LC-Fining hydrocracking system developed by C-E Lummus. Ebullated bed reactor 10 includes an inlet port 12 near the bottom, through which a feedstock 14 and pressurized hydrogen gas 16 are introduced, and an outlet port 18 at the top, through which hydroprocessed material 20 is withdrawn.

Reactor 10 further includes an expanded catalyst zone 22 comprising a heterogeneous catalyst 24 that is maintained in an expanded or fluidized state against the force of gravity by upward movement of liquid hydrocarbons and gas (schematically depicted as bubbles 25) through ebullated bed reactor 10. The lower end of expanded catalyst zone 22 is defined by a distributor grid plate 26, which separates expanded catalyst zone 22 from a lower heterogeneous catalyst free zone 28 located between the bottom of ebullated bed reactor 10 and distributor grid plate 26. Distributor grid plate 26 is configured to distribute the hydrogen gas and hydrocarbons evenly across the reactor and prevents heterogeneous catalyst 24 from falling by the force of gravity into lower heterogeneous catalyst free zone 28. The upper end of the expanded catalyst zone 22 is the height at which the downward force of gravity begins to equal or exceed the uplifting force of the upwardly moving feedstock and gas through ebullated bed reactor 10 as heterogeneous catalyst 24 reaches a given level of expansion or separation. Above expanded catalyst zone 22 is an upper heterogeneous catalyst free zone 30.

Hydrocarbons and other materials within the ebullated bed reactor 10 are continuously recirculated from upper heterogeneous catalyst free zone 30 to lower heterogeneous catalyst free zone 28 by means of a recycling channel 32 positioned in the center of ebullated bed reactor 10 connected to an ebullating pump 34 at the bottom of ebullated bed reactor 10. At the top of recycling channel 32 is a funnel-shaped recycle cup 36 through which feedstock is drawn from upper heterogeneous catalyst free zone 30. Material drawn downward through recycling channel 32 enters lower catalyst free zone 28 and then passes upwardly through distributor grid plate 26 and into expanded catalyst zone 22, where it is blended with freshly added feedstock 14 and hydrogen gas 16 entering ebullated bed reactor 10 through inlet port 12. Continuously circulating blended materials upward through the ebullated bed reactor 10 advantageously maintains heterogeneous catalyst 24 in an expanded or fluidized state within expanded catalyst zone 22, minimizes channeling, controls reaction rates, and keeps heat released by the exothermic hydrogenation reactions to a safe level.

Fresh heterogeneous catalyst 24 is introduced into ebullated bed reactor 10, such as expanded catalyst zone 22, through a catalyst inlet tube 38, which passes through the top of ebullated bed reactor 10 and directly into expanded catalyst zone 22. Spent heterogeneous catalyst 24 is withdrawn from expanded catalyst zone 22 through a catalyst withdrawal tube 40 that passes from a lower end of expanded catalyst zone 22 through distributor grid plate 26 and the bottom of ebullated bed reactor 10. It will be appreciated that the catalyst withdrawal tube 40 is unable to differentiate between fully spent catalyst, partially spent but active catalyst, and freshly added catalyst such that a random distribution of heterogeneous catalyst 24 is typically withdrawn from ebullated bed reactor 10 as "spent" catalyst.

Upgraded hydrocarbon material 20 withdrawn from ebullated bed reactor 10 can be introduced into a separator 42 (e.g., hot separator, inter-stage pressure differential separator, atmospheric distillation tower, or vacuum distillation tower). The separator 42 separates one or more volatile fractions (or distillates) 46 from a non-volatile fraction (or liquid) 48.

Figure 2B:
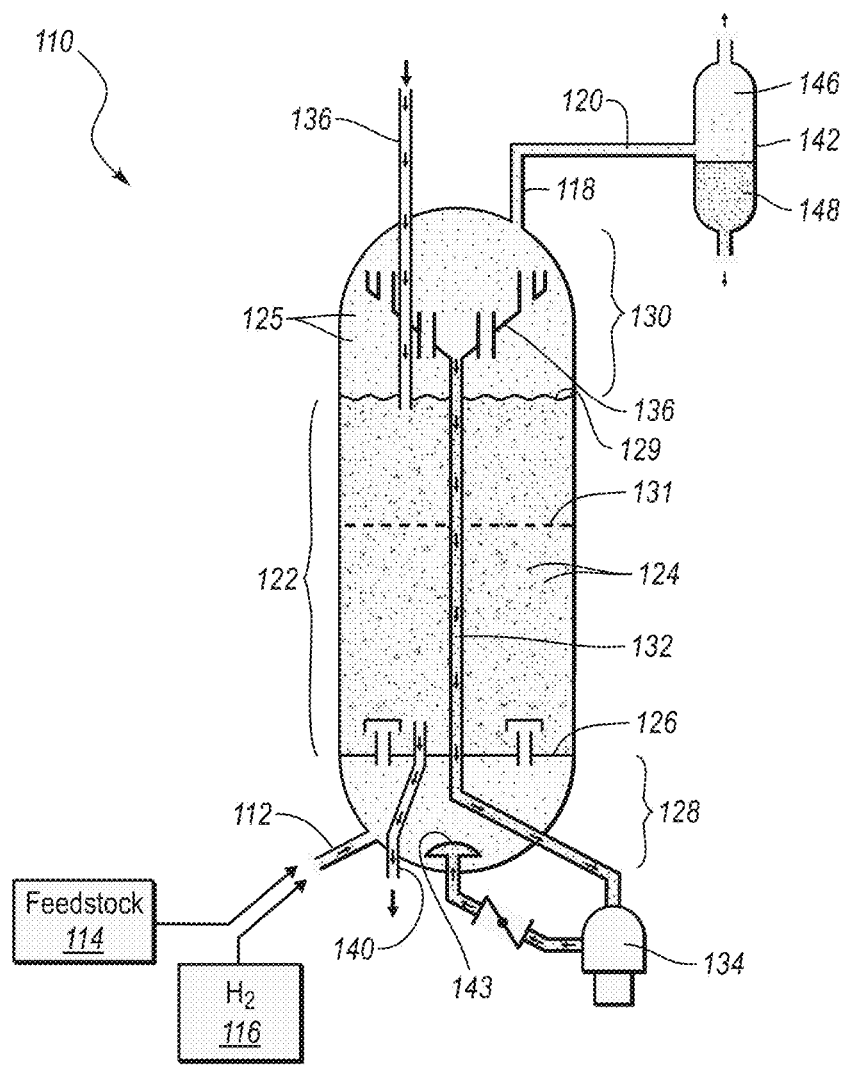

FIG. 2B schematically illustrates an ebullated bed reactor 110 used in the H-Oil hydrocracking system developed by Hydrocarbon Research Incorporated and currently licensed by Axens. Ebullated bed reactor 110 includes an inlet port 112, through which a heavy oil feedstock 114 and pressurized hydrogen gas 116 are introduced, and an outlet port 118, through which upgraded hydrocarbon material 120 is withdrawn. An expanded catalyst zone 122 comprising a heterogeneous catalyst 124 is bounded by a distributor grid plate 126, which separates expanded catalyst zone 122 from a lower catalyst free zone 128 between the bottom of reactor 110 and distributor grid plate 126, and an upper end 129, which defines an approximate boundary between expanded catalyst zone 122 and an upper catalyst free zone 130. Dotted boundary line 131 schematically illustrates the approximate level of heterogeneous catalyst 124 when not in an expanded or fluidized state.

Materials are continuously recirculated within ebullated bed reactor 110 by a recycling channel 132 connected to an ebullating pump 134 positioned outside of reactor 110. Materials are drawn through a funnel-shaped recycle cup 136 from upper catalyst free zone 130. Recycle cup 136 is spiral-shaped, which helps separate hydrogen bubbles 125 from recycled material 132 to prevent cavitation of ebullating pump 134. Recycled material 132 enters lower catalyst free zone 128, where it is blended with fresh feedstock 116 and hydrogen gas 118, and the mixture passes up through distributor grid plate 126 and into expanded catalyst zone 122. Fresh catalyst 124 is introduced into expanded catalyst zone 122 through a catalyst inlet tube 137, and spent catalyst 124 is withdrawn from expanded catalyst zone 122 through a catalyst discharge tube 140.

The main difference between the H-Oil ebullated bed reactor 110 and the LC-Fining ebullated bed reactor 10 is the location of the ebullating pump. Ebullating pump 134 in H-Oil reactor 110 is located external to the reaction chamber. The recirculating feedstock is introduced through a recirculation port 141 at the bottom of reactor 110. The recirculation port 141 includes a distributor 143, which aids in evenly distributing materials through lower catalyst free zone 128.

Upgraded hydrocarbon material 120 is shown being sent to a separator 142 (e.g. hot separator, pressure differential interstage separator, atmospheric distillation tower, or vacuum distillation tower), which separates one or more volatile fractions (or distillates) 146 from a non-volatile fraction (or liquid) 148.

Figure 2C:
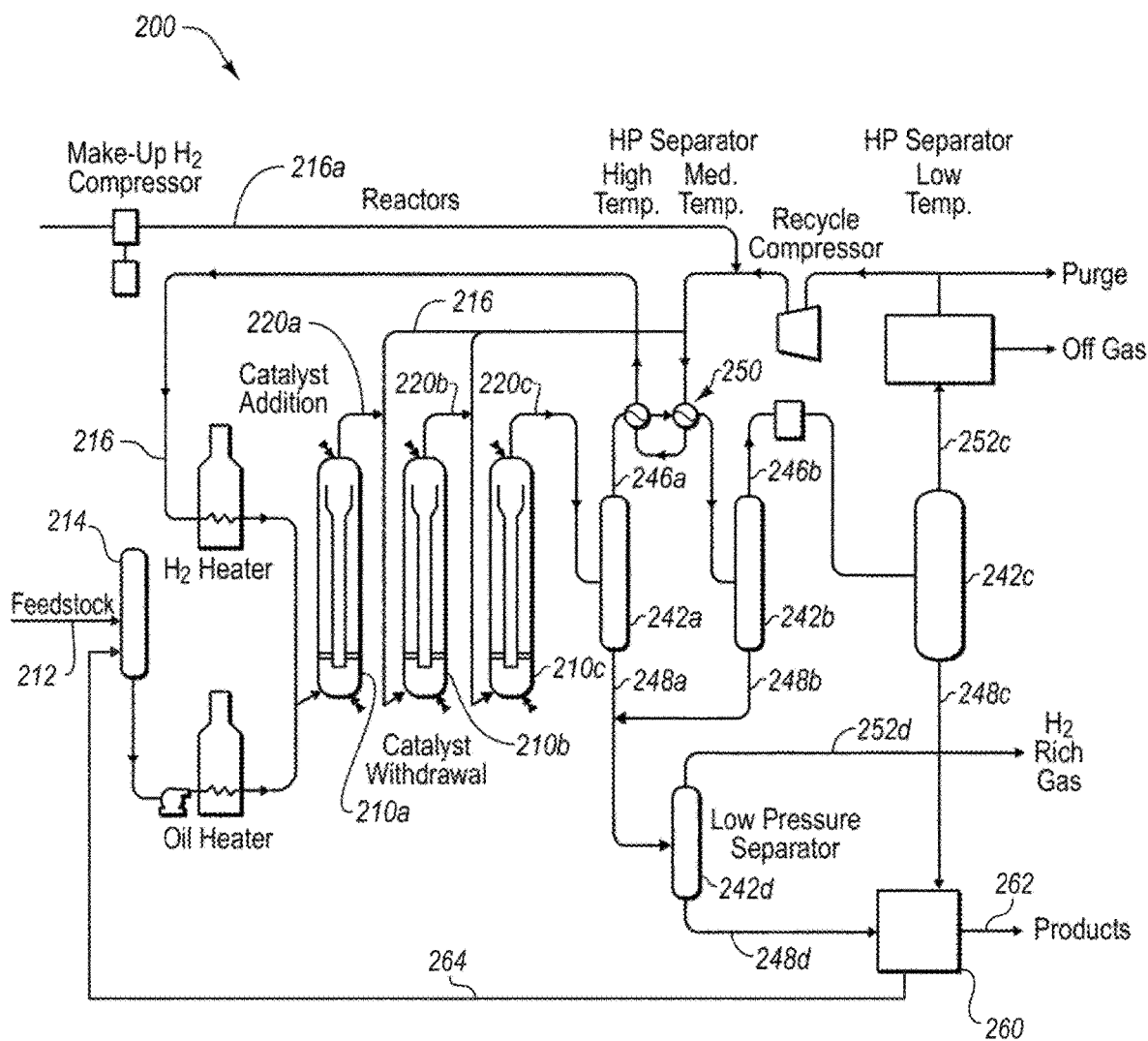
FIG. 2C schematically illustrates an exemplary ebullated bed hydroprocessing system comprising multiple ebullated bed reactors and recycling of vacuum tower bottoms.

FIG. 2C schematically illustrates an ebullated bed hydroprocessing system 200 comprising multiple ebullated bed reactors. Hydroprocessing system 200, an example of which is an LC-Fining or H-Oil hydroprocessing unit, may include three ebullated bed reactors 210 in series for upgrading a feedstock 212. Feedstock 212 from a surge tank 214 is pressurized, pre-heated, and introduced into a first ebullated bed reactor 210a together with hydrogen gas 216, both of which are passed through respective heaters prior to entering the reactor. Upgraded hydrocarbon material 220a from first ebullated bed reactor 210a is introduced together with additional hydrogen gas 216 into a second ebullated bed reactor 210b. Upgraded hydrocarbon material 220b from second ebullated bed reactor 210b is introduced together with additional hydrogen gas 216 into a third ebullated bed reactor 210c.

It should be understood that one or more interstage separators (not shown) can optionally be interposed between first and second ebullated bed reactors 210a, 210b and/or second and third ebullated bed reactors 210b, 210c, in order to remove lower boiling fractions and gases from a non-volatile fraction containing liquid hydrocarbons and residual dispersed metal sulfide catalyst particles. It can be desirable to remove lower alkanes, such as hexanes and heptanes, which are valuable fuel products but poor solvents for asphaltenes. Removing volatile materials between multiple reactors enhances production of valuable products and increases the solubility of asphaltenes in the liquid hydrocarbon material fed to downstream reactor(s). Both increase efficiency of the overall hydroprocessing system.

Upgraded hydrocarbon material 220c from third ebullated bed reactor 210c is sent to a high temperature separator 242a, which separates volatile and non-volatile fractions. A volatile fraction 246a passes through a heat exchanger 250, which removes heat that is used to preheat hydrogen gas 216 before it is fed into first ebullated bed reactor 210a. The somewhat cooled volatile fraction 246a is sent to a medium temperature separator 242b, which separates a remaining volatile fraction 246b from a resulting liquid fraction 248b that forms as a result of cooling by heat exchanger 250. Remaining volatile fraction 246b is sent downstream to a low temperature separator 242c for further separation into a gaseous fraction 252c and a degassed liquid fraction 248c.

A liquid fraction 248a from high temperature separator 242a is sent together with resulting liquid fraction 248b from medium temperature separator 242b to a low pressure separator 242d, which separates a hydrogen rich gas 252d from a degassed liquid fraction 248d, which is sent along with the degassed liquid fraction 248c from low temperature separator 242c to backend system 260, which includes one or more distillation towers, including a vacuum distillation tower, where the materials are fractionated into products 262 and a recycled stream of vacuum tower bottoms 264. The recycled stream of vacuum tower bottoms 264 may comprise some or all of the vacuum tower bottoms produced by backend system 260, with a portion of the vacuum tower bottoms optionally being removed as products 262 and not recycled.

Gaseous fraction 252c from low temperature separator 242c is purified into off-gas, purge gas, and hydrogen gas 216. Hydrogen gas 216 is compressed, mixed with make-up hydrogen gas 216a, and either passed through heat exchanger 250 and introduced into first ebullated bed reactor 210a together with feedstock 216 or introduced directly into second and third ebullated bed reactors 210b and 210b.

Figure 2D:
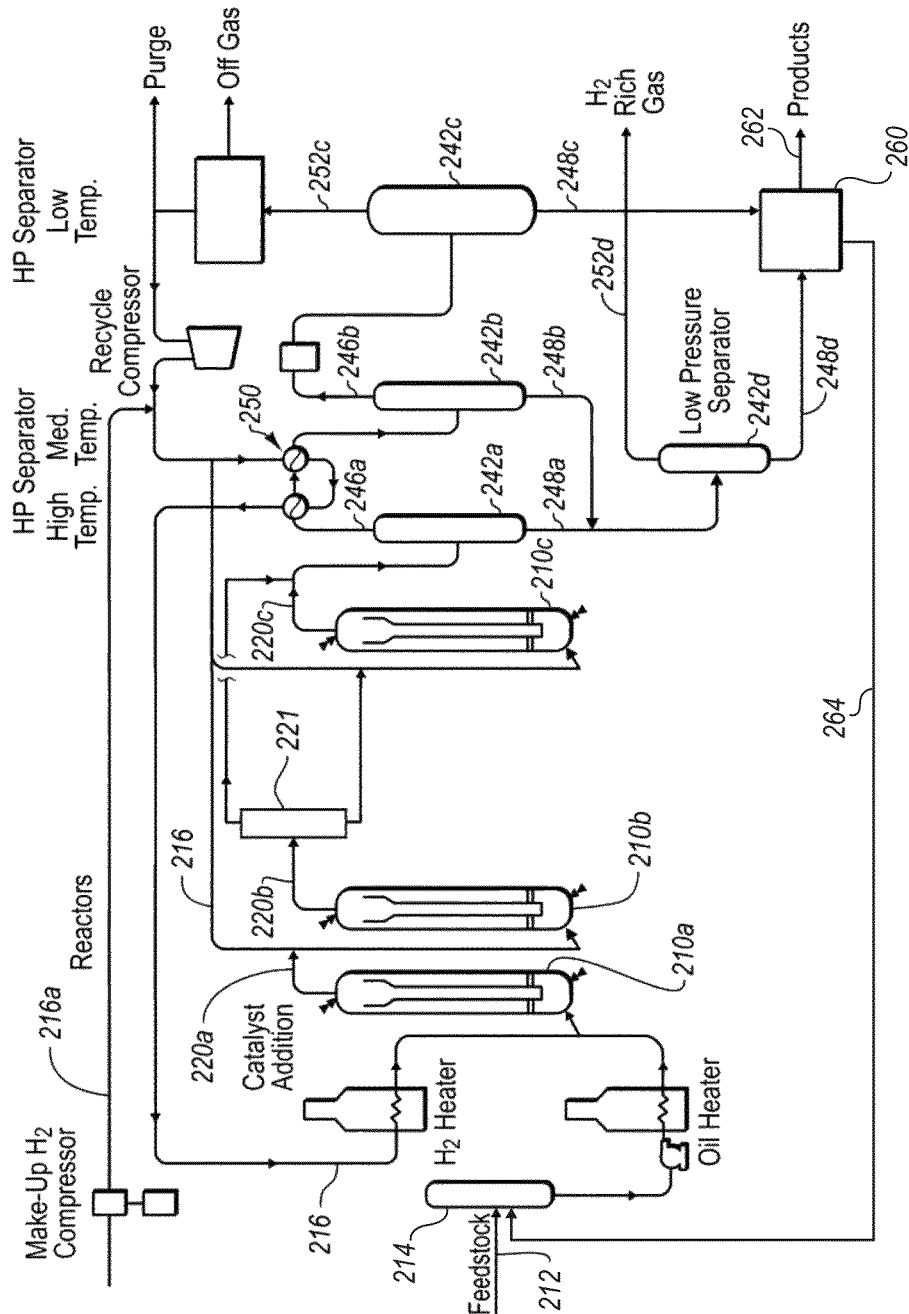
FIG. 2D schematically illustrates an exemplary ebullated bed hydroprocessing system comprising multiple ebullated bed reactors, similar to FIG. 2C, and an interstage separator between two of the reactors.

FIG. 2D schematically illustrates an ebullated bed hydroprocessing system 200 comprising multiple ebullated bed reactors, similar to the system illustrated in FIG. 2C, but showing an interstage separator 221 interposed between second and third reactors 210b, 210c (although interstage separator 221 (or other separator) may be interposed between first and second reactors 210a, 210b). As illustrated, effluent from second-stage reactor 210b enters interstage separator 221, which can be a high-pressure, high-temperature separator. The liquid fraction from separator 221 is combined with a portion of the recycle hydrogen from line 216 and then enters third-stage reactor 210c. The vapor fraction from interstage separator 221 bypasses third-stage reactor 210c, mixes with effluent from third-stage reactor 210c, and then passes into a high-pressure, high-temperature separator 242a.

This allows lighter, more-saturated components formed in the first two reactor stages to bypass third-stage reactor 210c. The benefits of this are (1) reduced vapor load on the third-stage reactor, which increases volume utilization of the third-stage reactor for converting the remaining heavy components, and (2) reduced concentration of "anti-solvent" components (saturates) which can destabilize (e.g., precipitate) asphaltenes in third-stage reactor 210c.

In preferred embodiments, the hydroprocessing systems are configured and operated to promote hydrocracking reactions rather than less severe hydroprocessing reactions, such as hydrotreating. Hydrocracking involves the breaking of carbon-carbon molecular bonds, such as reducing the molecular weight of larger hydrocarbon molecules and/or ring opening of aromatic compounds. Hydrotreating, on the other hand, mainly involves hydrogenation of unsaturated hydrocarbons, with minimal or no breaking of carbon-carbon molecular bonds.

To promote hydrocracking rather than mere hydrotreating reactions, the hydroprocessing reactor(s) are preferably operated at a temperature in a range of about 750° F. (399° C.) to about 860° F. (460° C.), more preferably in a range of about 780° F. (416° C.) to about 830° F. (443° C.), are preferably operated at a pressure in a range of about 1000 psig (6.9 MPa) to about 3000 psig (20.7 MPa), more preferably in a range of about 1500 psig (10.3 MPa) to about 2500 psig (17.2 MPa), and are preferably operated at a space velocity (e.g., Liquid Hourly Space Velocity, or LHSV, defined as the ratio of feed volume to reactor volume per hour) in a range of about 0.05 $hr^{-1}$ to about 0.45 $hr^{-1}$, more preferably in a range of about 0.1 $hr^{-1}$ to about 0.35 $hr^{-1}$.

The difference between hydrocracking and hydrotreating can also be expressed in terms of resid conversion (wherein hydrocracking results in the substantial conversion of higher boiling to lower boiling hydrocarbons, while hydrotreating does not). The hydroprocessing systems disclosed herein can result in resid conversion of about 40% to about 95%, preferably about 55% to about 90%. The preferred conversion range typically depends on the type of feedstock because of differences in processing difficulty between different feedstocks. In some cases, conversion can remain the same or it can be at least about 5% higher, preferably at least about 10% higher, compared to operating an ebullated bed reactor prior to upgrading to utilize a dual catalyst system as disclosed herein.

III. Upgrading an Ebullated Bed Hydroprocessing Reactor

FIGS. 3A, 3B, 3C, and 3D are flow diagrams which illustrate exemplary methods for upgrading an ebullated bed reactor to permit recycling of vacuum bottoms without recycle buildup of asphaltenes in the hydroprocessing system, such as in the vacuum bottoms.

Figure 3A:
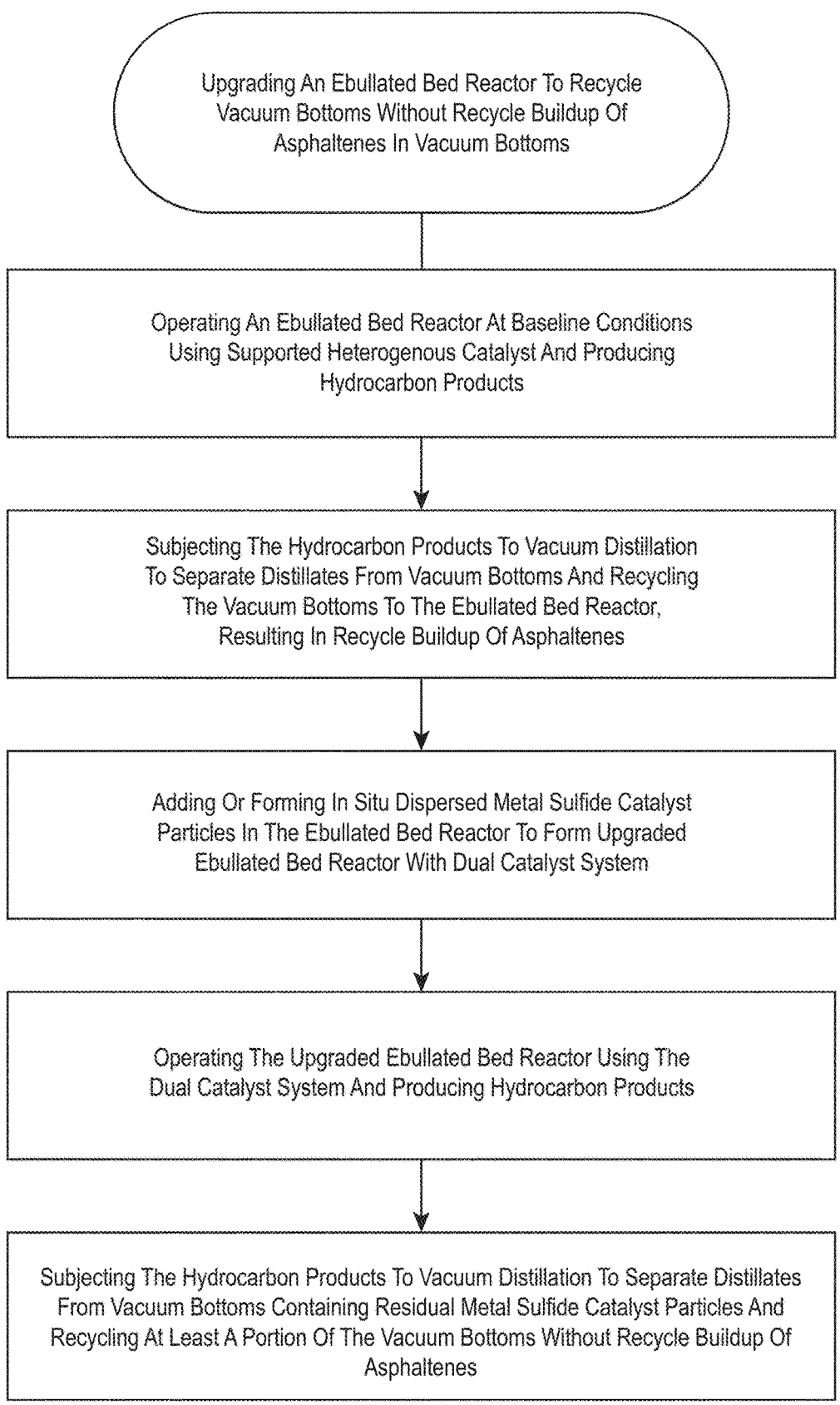
FIG. 3A is a flow diagram illustrating an exemplary method of upgrading an ebullated bed reactor to recycle vacuum bottoms without recycle buildup of asphaltenes in the vacuum bottoms.

FIG. 3A is a flow diagram illustrating an exemplary method of upgrading an ebullated bed reactor with recycling of vacuum bottoms without recycle buildup of asphaltenes comprising: (1) operating an ebullated bed reactor using a heterogeneous catalyst to hydroprocess heavy oil at baseline conditions, optionally with recycling of vacuum bottoms and recycle buildup of asphaltenes; (2) adding or forming in situ dispersed metal sulfide catalyst particles in the ebullated bed reactor to yield upgraded ebullated bed reactor with a dual catalyst system comprised of the heterogeneous catalyst and dispersed metal sulfide catalyst particles; (3) operating the upgraded ebullated bed reactor using the dual catalyst system to hydroprocess heavy oil to produce hydrocarbon products; (4) subjecting the hydrocarbon products to vacuum distillation and separating distillates from vacuum bottoms containing residual metal sulfide catalyst particles; and (5) recycling at least a portion of the vacuum bottoms containing residual metal sulfide catalyst particles into the upgraded ebullated bed reactor without recycle buildup of asphaltenes in the ebullated bed hydroprocessing system (e.g., vacuum bottoms).

According to some embodiments, the heterogeneous catalyst utilized when initially operating the ebullated bed reactor at baseline conditions is a commercially available catalyst typically used in ebullated bed reactor systems. To maximize efficiency, the baseline reactor conditions are advantageously at a level at which sediment formation and equipment fouling are maintained within acceptable levels. Some attempts have been made to increase absolute conversion of heavy oil and asphaltenes and increase total production of concerted products by recycling vacuum bottoms to the ebullated bed reactor. While recycling vacuum bottoms can theoretically work, it will often result in the recycle buildup of asphaltenes in the hydroprocessing system, which increases the risk of equipment fouling, often requiring more frequent shutdown and cleaning of the hydroprocessing reactor and related equipment, such as pipes, towers, heaters, heat exchangers, heterogeneous catalyst and/or separation equipment.

In order to permit more effective recycling of vacuum bottoms and eliminate or reduce recycle buildup of asphaltenes in the hydroprocessing system, the ebullated bed reactor is upgraded to use a dual catalyst system comprising a heterogeneous catalyst and dispersed metal sulfide catalyst particles. Operating the upgraded ebullated bed reactor using the dual catalyst system permits recycling of vacuum bottoms without recycle buildup of asphaltenes, or even a reduction of asphaltenes in the vacuum bottoms, even at one or more of higher conversion, higher temperature, and/or higher throughput compared to baseline conditions. This results in less equipment fouling and lower frequency of shutdowns and cleaning than when recycling vacuum bottoms with recycle buildup of asphaltenes.

The dispersed metal sulfide catalyst particles can be generated separately and then added to the ebullated bed reactor which, together with the heterogeneous catalyst, form the dual catalyst system. Alternatively or in addition, at least a portion of the dispersed metal sulfide catalyst particles can be generated in situ within the ebullated bed reactor. Additional details of the dispersed metal sulfide catalyst particles and how they are formed are set forth below.

Figure 3B:
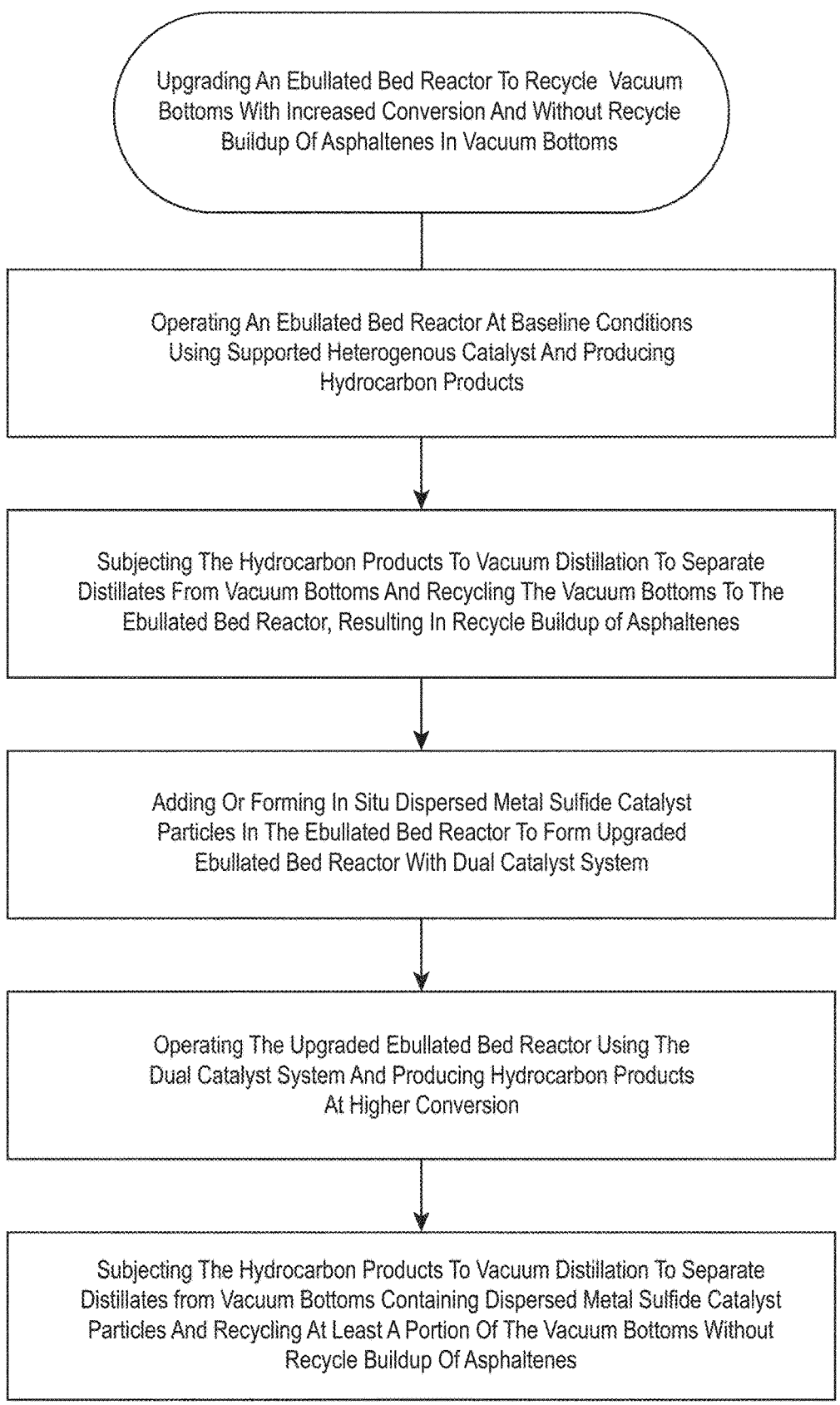
FIG. 3B is a flow diagram illustrating an exemplary method of upgrading an ebullated bed reactor to recycle vacuum bottoms with increased conversion compared to baseline conditions and without recycle buildup of asphaltenes in the vacuum bottoms.

FIG. 3B is a flow diagram illustrating another exemplary method of upgrading an ebullated bed reactor to permit recycling of vacuum bottoms at increased conversion without recycle buildup of asphaltenes comprising: (1) operating an ebullated bed reactor using a heterogeneous catalyst to hydroprocess heavy oil at baseline conditions, optionally with recycling of vacuum bottoms and recycle buildup of asphaltenes; (2) adding or forming in situ dispersed metal sulfide catalyst particles in the ebullated bed reactor to yield upgraded ebullated bed reactor with a dual catalyst system comprised of the heterogeneous catalyst and dispersed metal sulfide catalyst particles; (3) operating the upgraded ebullated bed reactor using the dual catalyst system to hydroprocess heavy oil to produce hydrocarbon products at higher conversion compared to baseline conditions; (4) subjecting the hydrocarbon products to vacuum distillation and separating distillates from vacuum bottoms containing residual metal sulfide catalyst particles; and (5) recycling at least a portion of the vacuum bottoms containing residual metal sulfide catalyst particles into the upgraded ebullated bed reactor without recycle buildup of asphaltenes in the ebullated bed hydroprocessing system (e.g., vacuum bottoms).

Figure 3C:
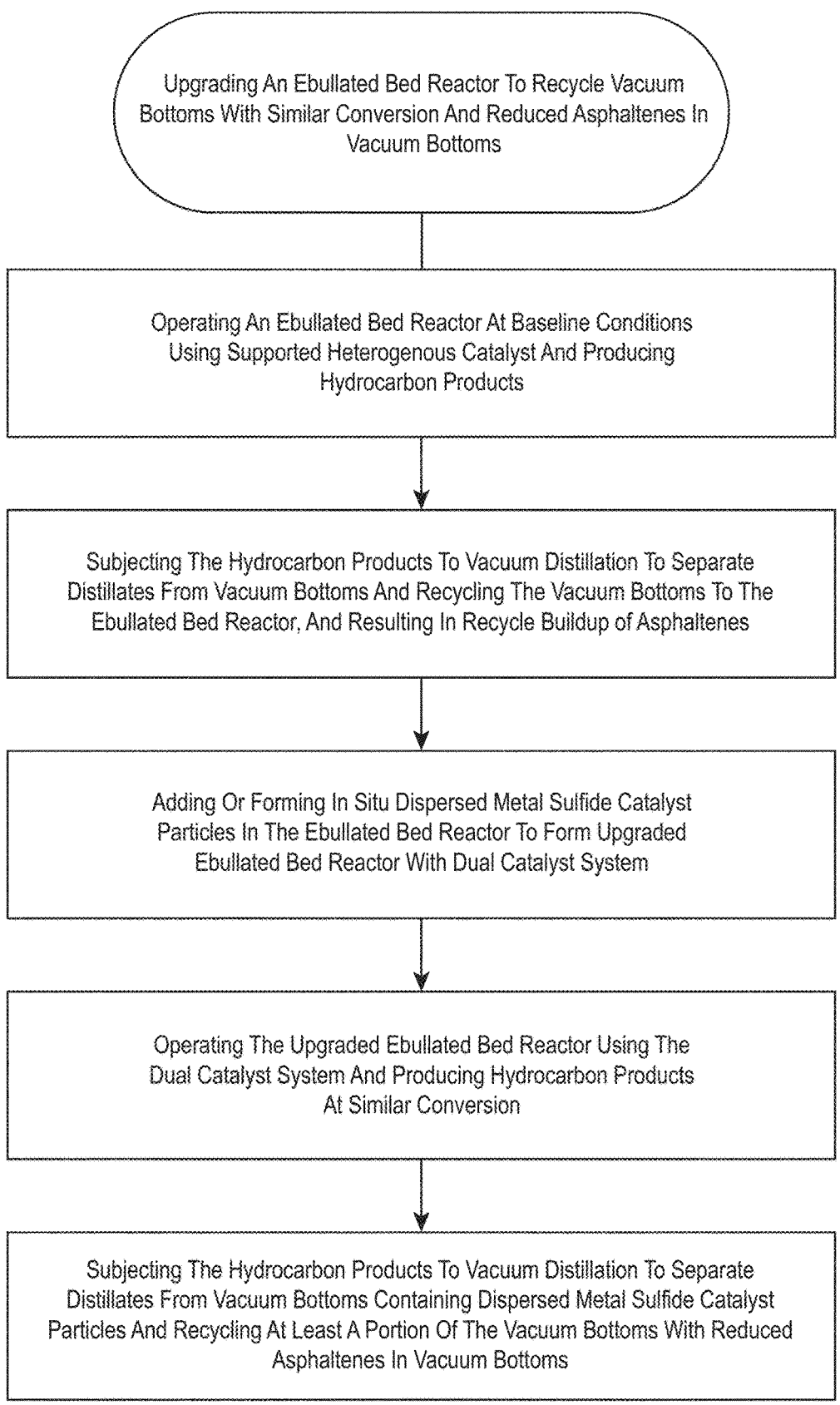
FIG. 3C is a flow diagram illustrating an exemplary method of upgrading an ebullated bed reactor to recycle vacuum bottoms with similar conversion compared to baseline conditions and reduced asphaltenes in the vacuum bottoms.

FIG. 3C is a flow diagram illustrating another exemplary method of upgrading an ebullated bed reactor to permit recycling of vacuum bottoms at similar conversion and reduced asphaltenes comprising: (1) operating an ebullated bed reactor using a heterogeneous catalyst to hydroprocess heavy oil at baseline conditions, optionally with recycling of vacuum bottoms and recycle buildup of asphaltenes; (2) adding or forming in situ dispersed metal sulfide catalyst particles in the ebullated bed reactor to yield upgraded ebullated bed reactor with a dual catalyst system comprised of the heterogeneous catalyst and dispersed metal sulfide catalyst particles; (3) operating the upgraded ebullated bed reactor using the dual catalyst system to hydroprocess heavy oil to produce hydrocarbon products at similar conversion compared to baseline conditions; (4) subjecting the hydrocarbon products to vacuum distillation and separating distillates from vacuum bottoms containing residual metal sulfide catalyst particles; and (5) recycling at least a portion of the vacuum bottoms containing residual metal sulfide catalyst particles into the upgraded ebullated bed reactor with reduced asphaltenes in the ebullated bed hydroprocessing system (e.g., vacuum bottoms).

Figure 3D:
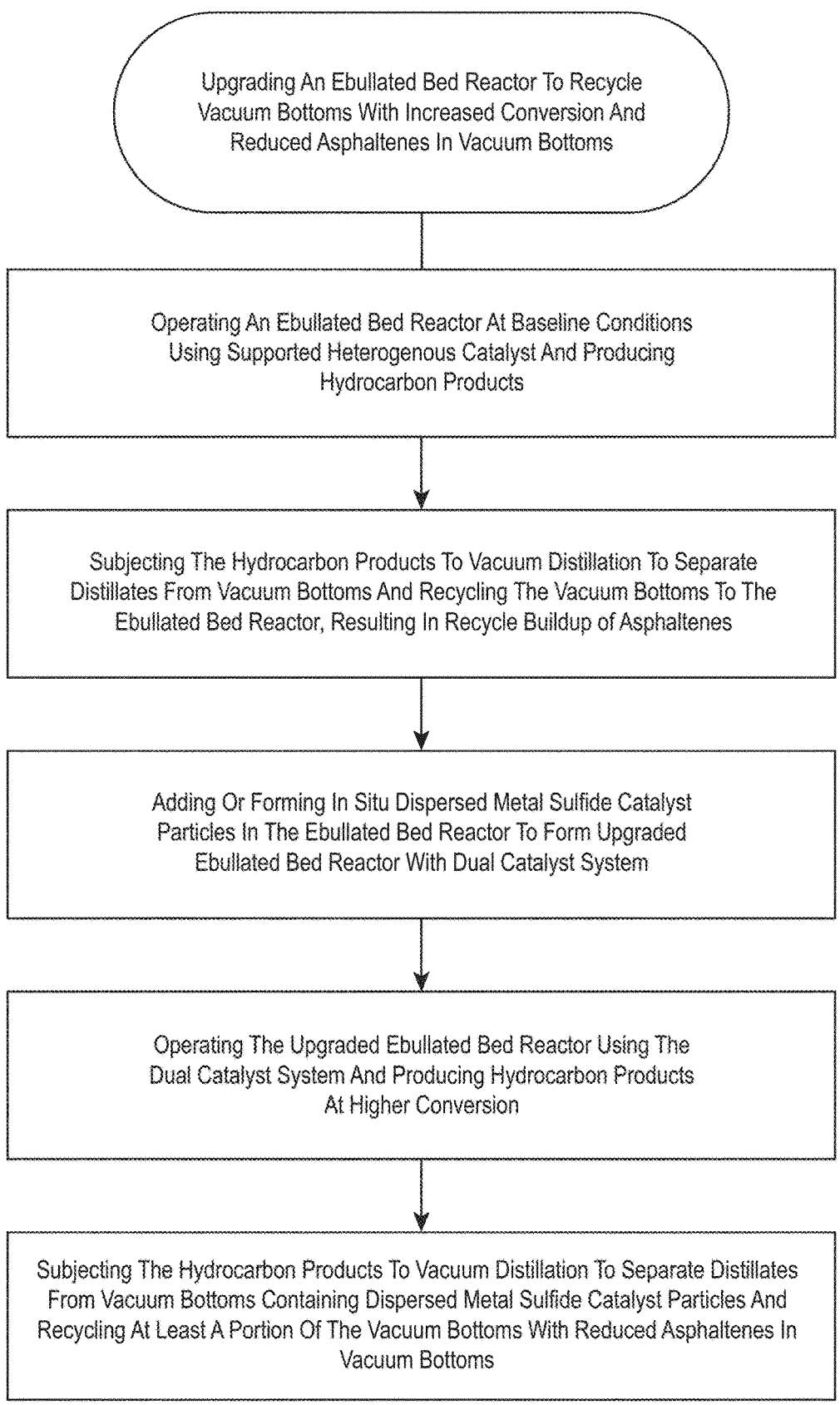
FIG. 3D is a flow diagram illustrating an exemplary method of upgrading an ebullated bed reactor to recycle vacuum bottoms with increased conversion compared to baseline conditions and reduced asphaltenes in the vacuum bottoms.

FIG. 3D is a flow diagram illustrating another exemplary method of upgrading an ebullated bed reactor to permit recycling of vacuum bottoms at higher conversion and reduced asphaltenes comprising: (1) operating an ebullated bed reactor using a heterogeneous catalyst to hydroprocess heavy oil at baseline conditions, optionally with recycling of vacuum bottoms and recycle buildup of asphaltenes; (2) adding or forming in situ dispersed metal sulfide catalyst particles in the ebullated bed reactor to yield upgraded ebullated bed reactor with a dual catalyst system comprised of the heterogeneous catalyst dispersed and metal sulfide catalyst particles; (3) operating the upgraded ebullated bed reactor using the dual catalyst system to hydroprocess heavy oil to produce hydrocarbon products at higher conversion compared to baseline conditions; (4) subjecting the hydrocarbon products to vacuum distillation and separating distillates from vacuum bottoms containing residual metal sulfide catalyst particles; and (5) recycling at least a portion of the vacuum bottoms containing residual metal sulfide catalyst particles into the upgraded ebullated bed reactor with reduced asphaltenes in the ebullated bed hydroprocessing system (e.g., vacuum bottoms).

In some embodiments, the production rate of converted products can be increased, when operating the upgraded ebullated bed reactor using the dual catalyst system and recycling vacuum bottoms, by at least one of: (i) higher temperature and higher conversion at same or similar throughput as when operating at the initial conditions; (ii) higher temperature and higher throughput at same or similar conversion as when operating at the initial conditions; or (iii) higher temperature, higher throughput, and higher conversion than when operating at the initial conditions.

In some embodiments, the vacuum bottoms can be recycled at a recycle ratio of from about 1% to about 50%, preferably from about 5% to about 40%, and more preferably from about 10% to about 30$. The recycle ratio can be expressed as a percentage determined by the ratio of vacuum bottoms recycle amount to the fresh feedstock amount, either on a volumetric or mass basis. These percentages indicate the flow rate of the vacuum bottoms as a volume percent of the fresh feedstock flow rate. The recycle ratio may also be readily converted to a mass percent basis, if the densities of the feedstock and vacuum bottoms are known.

In some embodiments, throughput can be increased by at least 2.5%, at least 5%, at least 10%, or at least 20% compared to baseline conditions.

In some embodiments, conversion can be increased by at least 2.5%, at least 5%, at least 7.5%, at least 10%, or at least 15% compared to baseline conditions.

In some embodiments, temperature can be increased by at least 2.5° C., at least 5° C., at least 7.5° C., or at least 10° C. compared to baseline conditions.

In some embodiments, after upgrading the ebullated bed reactor to use the dual catalyst system and recycling vacuum bottoms, the rate of equipment fouling may be decreased by at least 5%, 25%, 50%, or 75% compared to the rate of equipment fouling when operating at baseline conditions and/or when recycling vacuum bottoms without upgrading to use the dual catalyst system. In some embodiments, after upgrading to use the dual catalyst system the absolute concentration of asphaltenes in the hydroprocessing system can be lower, the same, or even higher than when operating the ebullated bed reactor at baseline conditions.

In some embodiments, the concentration of asphaltenes in the upgraded ebullated bed reactor can be reduced by at least about 5%, preferably by at least about 10%, more preferably by at least about 20% compared to the asphaltene concentration at baseline conditions with recycling of vacuum bottoms.

In some embodiments, the dispersed metal sulfide catalyst particles can be formed in situ within an entirety of a heavy oil feedstock that is added to an ebullated bed reactor. This can be accomplished by initially mixing a catalyst precursor with the entirety of the heavy oil feedstock to form a conditioned feedstock and thereafter heating the conditioned feedstock to decompose the catalyst precursor and cause or allow catalyst metal to react with sulfur and/or sulfur-containing molecules in and/or added to the heavy oil to form the dispersed metal sulfide catalyst particles.

The catalyst precursor can be oil-soluble and have a decomposition temperature in a range from about 100° C. (212° F.) to about 350° C. (662° F.), or in a range of about 150° C. (302° F.) to about 300° C. (572° F.), or in a range of about 175° C. (347° F.) to about 250° C. (482° F.). Example catalyst precursors include organometallic complexes or compounds, more specifically oil soluble compounds or complexes of transition metals and organic acids, having a decomposition temperature or range high enough to avoid substantial decomposition when mixed with a heavy oil feedstock under suitable mixing conditions. When mixing the catalyst precursor with a hydrocarbon oil diluent, it is advantageous to maintain the diluent at a temperature below which significant decomposition of the catalyst precursor occurs. One skilled in the art can, following the present disclosure, select a mixing temperature profile that results in intimate mixing of a selected precursor composition without substantial decomposition prior to formation of the dispersed metal sulfide catalyst particles.

Example catalyst precursors include, but are not limited to, molybdenum 2-ethylhexanoate, molybdenum octoate, molybdenum naphthenate, vanadium naphthenate, vanadium octoate, molybdenum hexacarbonyl, vanadium hexacarbonyl, and iron pentacarbonyl. Other catalyst precursors include molybdenum salts comprising a plurality of cationic molybdenum atoms and a plurality of carboxylate anions of at least 8 carbon atoms and that are at least one of (a) aromatic, (b) alicyclic, or (c) branched, unsaturated and aliphatic. By way of example, each carboxylate anion may have between 8 and 17 carbon atoms or between 11 and 15 carbon atoms. Examples of carboxylate anions that fit at least one of the foregoing categories include carboxylate anions derived from carboxylic acids selected from the group consisting of 3-cyclopentylpropionic acid, cyclohexanebutyric acid, biphenyl-2-carboxylic acid, 4-heptylbenzoic acid, 5-phenylvaleric acid, geranic acid (3,7-dimethyl-2,6-octadienoic acid), and combinations thereof.

In other embodiments, carboxylate anions suitable for use in making oil soluble, thermally stable, molybdenum catalyst precursor compounds are derived from carboxylic acids selected from the group consisting of 3-cyclopentylpropionic acid, cyclohexanebutyric acid, biphenyl-2-carboxylic acid, 4-heptylbenzoic acid, 5-phenylvaleric acid, geranic acid (3,7-dimethyl-2,6-octadienoic acid), 10-undecenoic acid, dodecanoic acid, and combinations thereof. It has been discovered that molybdenum catalyst precursors made using carboxylate anions derived from the foregoing carboxylic acids possess improved thermal stability.

Catalyst precursors with higher thermal stability can have a first decomposition temperature higher than 210° C., higher than about 225° C., higher than about 230° C., higher than about 240° C., higher than about 275° C., or higher than about 290° C. Such catalyst precursors can have a peak decomposition temperature higher than 250° C., or higher than about 260° C., or higher than about 270° C., or higher than about 280° C., or higher than about 290° C., or higher than about 330° C.

One of skill in the art can, following the present disclosure, select a mixing temperature profile that results in intimate mixing of a selected precursor composition without substantial decomposition prior to formation of the dispersed metal sulfide catalyst particles.

Whereas it is within the scope of the invention to directly blend the catalyst precursor with the heavy oil feedstock, care must be taken in such cases to mix the components for a time sufficient to thoroughly blend the catalyst precursor within the feedstock before substantial decomposition of the precursor composition has occurred. For example, U.S. Pat. No. 5,578,197 to Cyr et al., the disclosure of which is incorporated by reference, describes a method whereby molybdenum 2-ethyl hexanoate was mixed with bitumen vacuum tower residuum for 24 hours before the resulting mixture was heated in a reaction vessel to form the catalyst compound and to effect hydrocracking (see col. 10, lines 4-43). Whereas 24-hour mixing in a bench testing environment may be entirely acceptable, such long mixing times may make certain industrial operations prohibitively expensive. To ensure thorough mixing of the catalyst precursor within the heavy oil prior to heating to form the active catalyst, a series of mixing steps are performed by different mixing apparatus prior to heating the conditioned feedstock. These may include one or more low shear in-line mixers, followed by one or more high shear mixers, followed by a surge vessel and pump-around system, followed by one or more multi-stage high pressure pumps used to pressurize the feed stream prior to introducing it into a hydroprocessing reactor.

In some embodiments, the conditioned feedstock is preheated using a heating apparatus prior to entering the hydroprocessing reactor in order to form at least a portion of the dispersed metal sulfide catalyst particles in situ within the heavy oil before entering the reactor. In other embodiments, the conditioned feedstock is heated or further heated in the hydroprocessing reactor in order to form at least a portion of the dispersed metal sulfide catalyst particles in situ within the heavy oil while in the reactor.

In some embodiments, the dispersed metal sulfide catalyst particles can be formed in a multi-step process. For example, an oil soluble catalyst precursor composition can be premixed with a hydrocarbon diluent to form a diluted precursor mixture. Examples of suitable hydrocarbon diluents include, but are not limited to, vacuum gas oil (which typically has a nominal boiling range of 360-524° C.) (680-975° F.), decant oil or cycle oil (which typically has a nominal boiling range of 360°-550° C.) (680-1022° F.), and gas oil (which typically has a nominal boiling range of 200°-360° C.) (392-680° F.), a portion of the heavy oil feedstock, and other hydrocarbons that nominally boil at a temperature higher than about 200° C.

The ratio of catalyst precursor to hydrocarbon oil diluent used to make the diluted precursor mixture can be in a range of about 1:500 to about 1:1, or in a range of about 1:150 to about 1:2, or in a range of about 1:100 to about 1:5 (e.g., 1:100, 1:50, 1:30, or 1:10).

The amount of catalyst metal (e.g., molybdenum) in the diluted precursor mixture is preferably in a range of about 100 ppm to about 7000 ppm by weight of the diluted precursor mixture, more preferably in a range of about 300 ppm to about 4000 ppm by weight of the diluted precursor mixture.

The catalyst precursor is advantageously mixed with the hydrocarbon diluent below a temperature at which a significant portion of the catalyst precursor composition decomposes. The mixing may be performed at temperature in a range of about 25° C. (77° F.) to about 250° C. (482° F.), or in range of about 50° C. (122° F.) to about 200° C. (392° F.), or in a range of about 75° C. (167° F.) to about 150° C. (302° F.), to form the diluted precursor mixture. The temperature at which the diluted precursor mixture is formed may depend on the decomposition temperature and/or other characteristics of the catalyst precursor that is utilized and/or characteristics of the hydrocarbon diluent, such as viscosity.

The catalyst precursor is preferably mixed with the hydrocarbon oil diluent for a time period in a range of about 0.1 second to about 5 minutes, or in a range of about 0.5 second to about 3 minutes, or in a range of about 1 second to about 1 minute. The actual mixing time is dependent, at least in part, on the temperature (i.e., which affects the viscosity of the fluids) and mixing intensity. Mixing intensity is dependent, at least in part, on the number of stages e.g., for an in-line static mixer.

Pre-blending the catalyst precursor with a hydrocarbon diluent to form a diluted precursor mixture which is then blended with the heavy oil feedstock greatly aids in thoroughly and intimately blending the catalyst precursor within the feedstock, particularly in the relatively short period of time required for large-scale industrial operations. Forming a diluted precursor mixture shortens the overall mixing time by (1) reducing or eliminating differences in solubility between a more polar catalyst precursor and a more hydrophobic heavy oil feedstock, (2) reducing or eliminating differences in rheology between the catalyst precursor and heavy oil feedstock, and/or (3) breaking up catalyst precursor molecules to form a solute within the hydrocarbon diluent that is more easily dispersed within the heavy oil feedstock.

The diluted precursor mixture is then combined with a heavy oil feedstock and mixed for a time sufficient and in a manner so as to disperse the catalyst precursor throughout the heavy oil to form a conditioned feedstock in which the catalyst precursor is thoroughly mixed within the heavy oil prior to thermal decomposition and formation of the active metal sulfide catalyst particles. In order to obtain sufficient mixing of the catalyst precursor within the heavy oil feedstock, the diluted precursor mixture and heavy oil feedstock are advantageously mixed for a time period in a range of about 0.1 second to about 5 minutes, or in a range from about 0.5 second to about 3 minutes, or in a range of about 1 second to about 1 minute. Increasing the vigorousness and/or shearing energy of the mixing process generally reduce the time required to effect thorough mixing.

Examples of mixing apparatus that can be used to effect thorough mixing of the catalyst precursor and/or diluted precursor mixture with heavy oil include, but are not limited to, high shear mixing such as mixing created in a vessel with a propeller or turbine impeller; multiple static in-line mixers; multiple static in-line mixers in combination with in-line high shear mixers; multiple static in-line mixers in combination with in-line high shear mixers followed by a surge vessel; combinations of the above followed by one or more multi-stage centrifugal pumps; and one or more multi-stage centrifugal pumps. According to some embodiments, continuous rather than batch-wise mixing can be carried out using high energy pumps having multiple chambers within which the catalyst precursor composition and heavy oil feedstock are churned and mixed as part of the pumping process itself. The foregoing mixing apparatus may also be used for the pre-mixing process discussed above in which the catalyst precursor is mixed with the hydrocarbon diluent to form the catalyst precursor mixture.

In the case of heavy oil feedstocks that are solid or extremely viscous at room temperature, such feedstocks may advantageously be heated in order to soften them and create a feedstock having sufficiently low viscosity so as to allow good mixing of the oil soluble catalyst precursor into the feedstock composition. In general, decreasing the viscosity of the heavy oil feedstock will reduce the time required to effect thorough and intimate mixing of the oil soluble precursor composition within the feedstock.

The heavy oil feedstock and catalyst precursor and/or diluted precursor mixture are advantageously mixed at a temperature in a range of about 25° C. (77° F.) to about 350° C. (662° F.), or in a range of about 50° C. (122° F.) to about 300° C. (572° F.), or in a range of about 75° C. (167° F.) to about 250° C. (482° F.) to yield a conditioned feedstock.

In the case where the catalyst precursor is mixed directly with the heavy oil feedstock without first forming a diluted precursor mixture, it may be advantageous to mix the catalyst precursor and heavy oil feedstock for a time period in a range of about 0.2 second to about 10 minutes, or in a range from about 1 second to about 6 minutes, or in a range of about 2 seconds to about 2 minutes. It may also be advantageous to mix the catalyst precursor and heavy oil feedstock below a temperature at which a significant portion of the catalyst precursor composition decomposes.

In the case where the catalyst precursor is premixed with a hydrocarbon diluent to form a diluted precursor mixture, which is thereafter mixed with the heavy oil feedstock, it may be permissible for the heavy oil feedstock to be at or above the decomposition temperature of the catalyst precursor. In some cases the hydrocarbon diluent shields the individual catalyst precursor molecules and prevents them from agglomerating to form larger particles, temporarily insulates the catalyst precursor molecules from heat from the heavy oil during mixing, and facilitates dispersion of the catalyst precursor molecules sufficiently quickly throughout the heavy oil feedstock before decomposing to liberate metal. In addition, additional heating of the feedstock may be necessary to liberate hydrogen sulfide from sulfur-bearing molecules in the heavy oil to form the metal sulfide catalyst particles. In this way, progressive dilution of the catalyst precursor permits a high level of dispersion within the heavy oil feedstock, resulting in the formation of highly dispersed metal sulfide catalyst particles, even where the feedstock is at a temperature above the decomposition temperature of the catalyst precursor.

After the catalyst precursor has been well-mixed throughout the heavy oil to yield a conditioned feedstock, this composition is heated to cause decomposition of the catalyst precursor, which liberates catalyst metal therefrom, cause or allow catalyst metal to react with sulfur within and/or added to the heavy oil, and form the active metal sulfide catalyst particles. Metal from the catalyst precursor may initially form a metal oxide, which then reacts with sulfur in the heavy oil to yield a metal sulfide compound that forms the final active catalyst. In the case where the heavy oil feedstock includes sufficient or excess sulfur, the final activated catalyst may be formed in situ by heating the heavy oil feedstock to a temperature sufficient to liberate sulfur therefrom. In some cases, sulfur may be liberated at the same temperature that the precursor composition decomposes. In other cases, further heating to a higher temperature may be required.

If the catalyst precursor is thoroughly mixed throughout the heavy oil, at least a substantial portion of the liberated metal ions will be sufficiently sheltered or shielded from other metal ions so that they can form a molecularly-dispersed catalyst upon reacting with sulfur to form the metal sulfide compound. Under some circumstances, minor agglomeration may occur, yielding colloidal-sized catalyst particles. However, it is believed that taking care to thoroughly mix the catalyst precursor throughout the feedstock prior to thermal decomposition of the catalyst precursor may yield individual catalyst molecules rather than colloidal particles. Simply blending, while failing to sufficiently mix, the catalyst precursor with the feedstock typically causes formation of large agglomerated metal sulfide compounds that are micron-sized or larger.

In order to form dispersed metal sulfide catalyst particles, the conditioned feedstock is heated to a temperature in a range of about 275° C. (527° F.) to about 450° C. (842° F.), or in a range of about 310° C. (590° F.) to about 430° C. (806° F.), or in a range of about 330° C. (626° F.) to about 410° C. (770° F.).

The initial concentration of catalyst metal in the heavy oil provided by dispersed metal sulfide catalyst particles can be in a range of about 1 ppm to about 500 ppm by weight of the heavy oil feedstock, or in a range of about 5 ppm to about 300 ppm, or in a range of about 10 ppm to about 100 ppm. The catalyst may become more concentrated as volatile fractions are removed from a resid fraction. Recycling of vacuum bottoms can be a source of dispersed metal sulfide catalyst particles, which can maintain a desired concentration in the ebullated bed reactor with decreased use of catalyst precursor, or it can increase the concentration of dispersed metal sulfide catalyst particles, which can help hydroprocessing the additional asphaltenes provided by the recycled vacuum bottoms.

In the case where the heavy oil feedstock includes a significant quantity of asphaltene molecules, the dispersed metal sulfide catalyst particles may preferentially associate with, or remain in close proximity to, the asphaltene molecules. Asphaltene molecules can have a greater affinity for the metal sulfide catalyst particles since asphaltene molecules are generally more hydrophilic and less hydrophobic than other hydrocarbons contained within heavy oil. Because the metal sulfide catalyst particles tend to be very hydrophilic, the individual particles or molecules will tend to migrate toward more hydrophilic moieties or molecules within the heavy oil feedstock.

While the highly polar nature of metal sulfide catalyst particles causes or allows them to associate with asphaltene molecules, it is the general incompatibility between the highly polar catalyst compounds and hydrophobic heavy oil that necessitates the aforementioned intimate or thorough mixing of catalyst precursor composition within the heavy oil prior to decomposition and formation of the active catalyst particles. Because metal catalyst compounds are highly polar, they cannot be effectively dispersed within heavy oil if added directly thereto. In practical terms, forming smaller active catalyst particles results in a greater number of catalyst particles that provide more evenly distributed catalyst sites throughout the heavy oil.

IV. Upgraded Ebullated Bed Reactor

Figure 4:
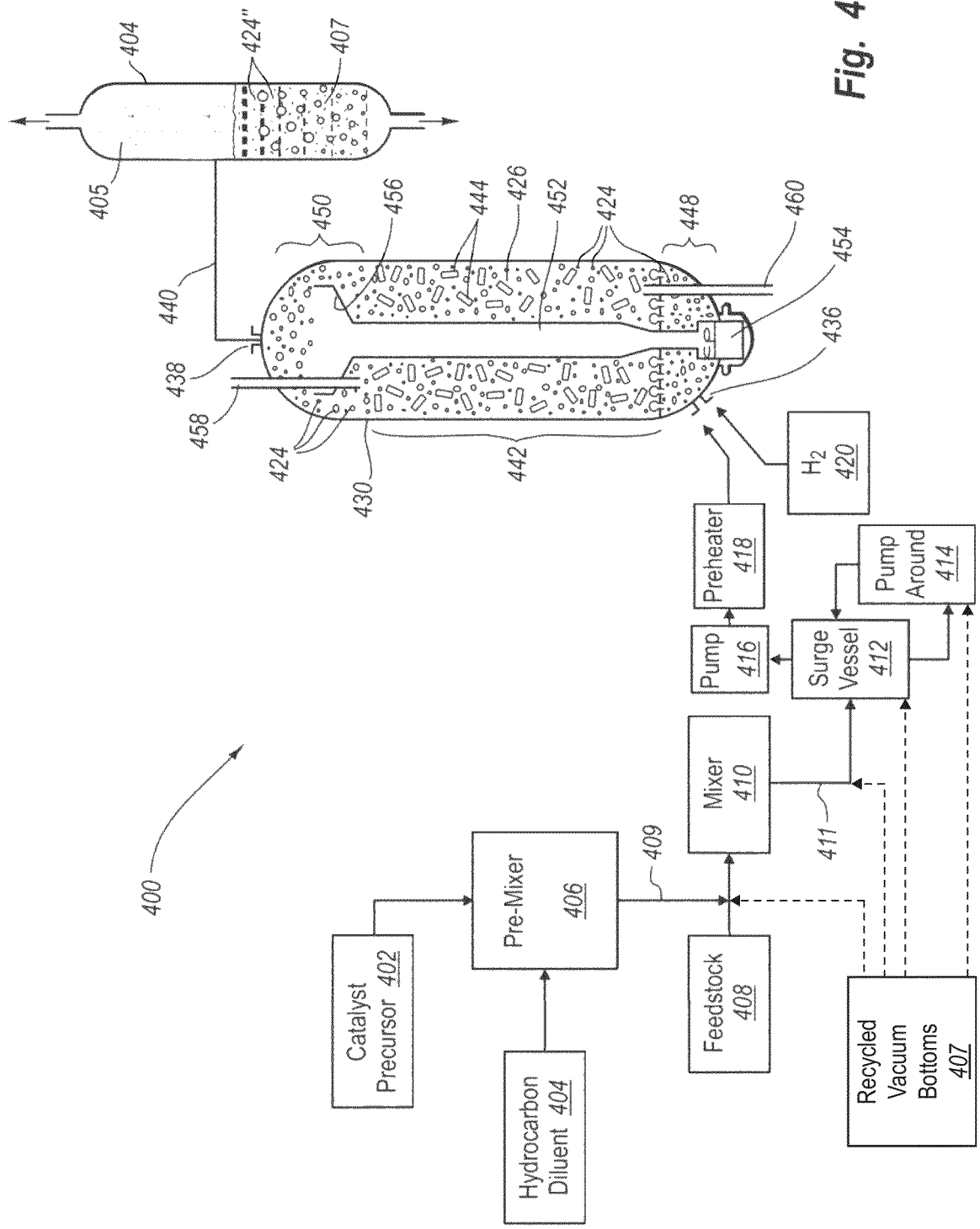
FIG. 4 schematically illustrates an exemplary ebullated bed hydroprocessing system using a dual catalyst system.

FIG. 4 schematically illustrates an example upgraded ebullated bed hydroprocessing system 400 that can be used in the disclosed methods and systems. Ebullated bed hydroprocessing system 400 includes an upgraded ebullated bed reactor 430 and a hot separator 404 (or other separator, such as a distillation tower). To create upgraded ebullated bed reactor 430, a catalyst precursor 402 is initially pre-blended with a hydrocarbon diluent 404 in one or more mixers 406 to form a catalyst precursor mixture 409. Catalyst precursor mixture 409 is added to feedstock 408 and blended with the feedstock in one or more mixers 410 to form conditioned feedstock 411. Conditioned feedstock is fed to a surge vessel 412 with pump around loop 414 to cause further mixing and dispersion of the catalyst precursor within the conditioned feedstock.

Upgraded ebullated bed hydroprocess system includes means for the addition of recycled vacuum bottoms 407. The exact location of addition can be selected based on the configuration and/or needs of a particular hydroprocessing system. In some embodiments, the recycled vacuum bottoms 407 can be added to the feedstock 408 upstream from at least one of the one or more mixers 410, downstream from at least one of the one or more mixers 410, into the surge vessel 412, or into the pump around loop 414. In some embodiments, the recycled vacuum bottoms 407 can be added at multiple locations.

The conditioned feedstock from surge vessel 412 is pressurized by one or more pumps 416, passed through a pre-heater 418, and fed into ebullated bed reactor 430 together with pressurized hydrogen gas 420 through an inlet port 436 located at or near the bottom of ebullated bed reactor 430. Heavy oil material 426 in ebullated bed reactor 430 contains dispersed metal sulfide catalyst particles, schematically depicted as catalyst particles 424.

Heavy oil feedstock 408 may comprise any desired fossil fuel feedstock and/or fraction thereof including, but not limited to, one or more of heavy crude, oil sands bitumen, bottom of the barrel fractions from crude oil, atmospheric tower bottoms, vacuum tower bottoms, coal tar, liquefied coal, and other resid fractions. In some embodiments, heavy oil feedstock 408 can include a significant fraction of high boiling point hydrocarbons (i.e., nominally at or above 343° C. (650° F.), more particularly nominally at or above about 524° C. (975° F.)) and/or asphaltenes. Asphaltenes are complex hydrocarbon molecules that include a relatively low ratio of hydrogen to carbon that is the result of a substantial number of condensed aromatic and naphthenic rings with paraffinic side chains (See FIG. 1). Sheets consisting of the condensed aromatic and naphthenic rings are held together by heteroatoms such as sulfur or nitrogen and/or polymethylene bridges, thio-ether bonds, and vanadium and nickel complexes. The asphaltene fraction also contains a higher content of sulfur and nitrogen than does crude oil or the rest of the vacuum resid, and it also contains higher concentrations of carbon-forming compounds (i.e., that form coke precursors and sediment).

Ebullated bed reactor 430 further includes an expanded catalyst zone 442 comprising a heterogeneous catalyst 444. A lower heterogeneous catalyst free zone 448 is located below expanded catalyst zone 442, and an upper heterogeneous catalyst free zone 450 is located above expanded catalyst zone 442. Dispersed metal sulfide catalyst particles 424 are dispersed throughout material 426 within ebullated bed reactor 430, including expanded catalyst zone 442, heterogeneous catalyst free zones 448, 450, 452 thereby being available to promote upgrading reactions within what constituted catalyst free zones in the ebullated bed reactor prior to being upgraded to include the dual catalyst system.

To promote hydrocracking reactions rather than mere hydrotreating reactions, the hydroprocessing reactor(s) are preferably operated at a temperature in a range of about 750° F. (399° C.) to about 860° F. (460° C.), more preferably in a range of about 780° F. (416° C.) to about 830° F. (443° C.), are preferably operated at a pressure in a range of about 1000 psig (6.9 MPa) to about 3000 psig (20.7 MPa), more preferably in a range of about 1500 psig (10.3 MPa) to about 2500 psig (17.2 MPa), and are preferably operated at a space velocity (LHSV) in a range of about 0.05 $hr^{-1}$ to about 0.45 $hr^{-1}$, more preferably in a range of about 0.1 $hr^{-1}$ to about 0.35 $hr^{-1}$. The difference between hydrocracking and hydrotreating can also be expressed in terms of resid conversion (wherein hydrocracking results in the substantial conversion of higher boiling to lower boiling hydrocarbons, while hydrotreating does not). The hydroprocessing systems disclosed herein can result in a resid conversion in a range of about 40% to about 95%, preferably in a range of about 55% to about 90%. The preferred conversion range typically depends on the type of feedstock because of differences in processing difficulty between different feedstocks. Typically, conversion will be at least about 5% higher, preferably at least about 10% higher, compared to operating an ebullated bed reactor prior to upgrading to utilize a dual catalyst system as disclosed herein.

Material 426 in ebullated bed reactor 430 is continuously recirculated from upper heterogeneous catalyst free zone 450 to lower heterogeneous catalyst free zone 448 by means of a recycling channel 452 connected to an ebullating pump 454. At the top of recycling channel 452 is a funnel-shaped recycle cup 456 through which material 426 is drawn from upper heterogeneous catalyst free zone 450. Recycled material 426 is blended with fresh conditioned feedstock 411 and hydrogen gas 420.

Fresh heterogeneous catalyst 444 is introduced into ebullated bed reactor 430 through a catalyst inlet tube 458, and spent heterogeneous catalyst 444 is withdrawn through a catalyst withdrawal tube 460. Whereas the catalyst withdrawal tube 460 is unable to differentiate between fully spent catalyst, partially spent but active catalyst, and fresh catalyst, the existence of dispersed metal sulfide catalyst particles 424 provides additional catalytic activity, within expanded catalyst zone 442, recycle channel 452, and lower and upper heterogeneous catalyst free zones 448, 450. The addition of hydrogen to hydrocarbons outside of heterogeneous catalyst 444 minimizes formation of sediment and coke precursors, which are often responsible for deactivating the heterogeneous catalyst.

Ebullated bed reactor 430 further includes an outlet port 438 at or near the top through which converted material 440 is withdrawn. Converted material 440 is introduced into hot separator or distillation tower 404. Hot separator or distillation tower 404 separates one or more volatile fractions 405, which is/are withdrawn from the top of hot separator 404, from a resid fraction 407, which is withdrawn from a bottom of hot separator or distillation tower 404. Resid fraction 407 contains residual metal sulfide catalyst particles, schematically depicted as catalyst particles 424. If desired, at least a portion of resid fraction 407 can be recycled back to ebullated bed reactor 430 in order to form part of the feed material and to supply additional metal sulfide catalyst particles. Alternatively, resid fraction 407 can be further processed using downstream processing equipment, such as another ebullated bed reactor. In that case, separator 404 can be an interstage separator.

In some embodiments, operating the upgraded ebullated bed reactor using a dual catalyst system and with recycling of vacuum bottoms can result in the same or reduced equipment fouling compared to operating the ebullated bed reactor at baseline conditions with only a heterogeneous catalyst rather than the dual catalyst system. For example, the rate of equipment fouling when operating the upgraded ebullated bed reactor using a dual catalyst system and with recycling of vacuum bottoms may result in a frequency of heat exchanger shutdowns and/or distillation tower shutdowns for cleanout that is equal to or less than when operating the ebullated bed reactor at baseline conditions.

In addition or alternatively, the rate of equipment fouling when operating of the upgraded ebullated bed reactor using a dual catalyst system and with recycling of vacuum bottoms may result in a frequency of changes or cleaning of filters and strainers that is equal or less than when operating the ebullated bed reactor at baseline conditions.

In addition or alternatively, the rate of equipment fouling when operating of the upgraded ebullated bed reactor using a dual catalyst system and with recycling of vacuum bottoms may result in a frequency of switches to spare heat exchangers that is equal or less than when initially operating the ebullated bed reactor.

In addition or alternatively, the rate of equipment fouling when operating of the upgraded ebullated bed reactor using a dual catalyst system and with recycling of vacuum bottoms may result in a reduced rate of decreasing skin temperatures in equipment selected from one or more of heat exchangers, separators, or distillation towers than when initially operating the ebullated bed reactor.

In addition or alternatively, the rate of equipment fouling when operating of the upgraded ebullated bed reactor using a dual catalyst system and with recycling of vacuum bottoms may result in a reduced rate of increasing furnace tube metal temperatures than when initially operating the ebullated bed reactor.

In addition or alternatively, the rate of equipment fouling when operating of the upgraded ebullated bed reactor using a dual catalyst system and with recycling of vacuum bottoms may result in a reduced rate of increasing calculated fouling resistance factors for heat exchangers than when initially operating the ebullated bed reactor.

V. Experimental Studies and Results

A series of experiments were conducted using a two-stage ebullated bed pilot plant. These tests included both non-recycling and recycling of vacuum bottoms to the ebullated bed reactor, and were conducted at three different levels of dispersed catalyst usage. In other respects, the tests were identical, using the same vacuum residue feedstock of Russian Export Blend (Urals) type, the same solid supported ebullated bed catalyst, and the same process operating parameters (pressure, space velocity, etc). The tests demonstrated how the recycle build-up of harmful asphaltenes in an ebullated bed process with recycling of vacuum bottoms may be prevented by the use of a dual catalyst system.

Figure 5:
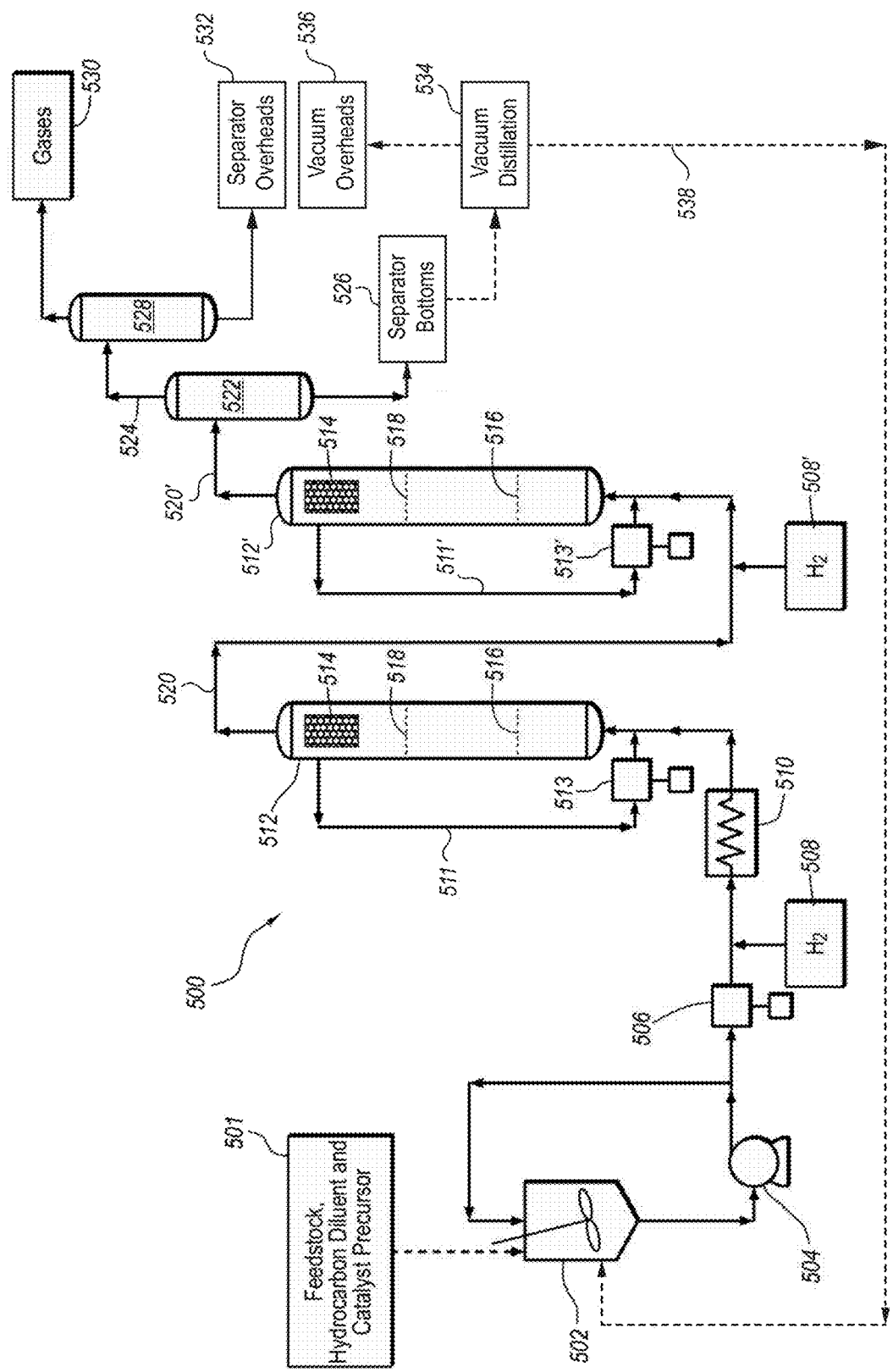
FIG. 5 schematically illustrates a pilot scale ebullated bed hydroprocessing system configured to employ either a heterogeneous catalyst by itself or a dual catalyst system including a heterogeneous catalyst and dispersed metal sulfide particles.

As schematically illustrated in FIG. 5, a pilot plant 500 with two ebullated bed reactors 512, 512' connected in series were used to compare the use of a heterogeneous catalyst by itself and a dual catalyst system comprised of the heterogeneous catalyst in combination with dispersed metal sulfide catalyst particles (i.e., dispersed molybdenum disulfide catalyst particles).

Pilot plant 500 more particularly includes a mixing device 502 for blending a catalyst precursor (e.g., molybdenum 2-ethylhexanoate, 15% molybdenum by weight) with a heavy oil feedstock (collectively depicted as 501) to form a conditioned feedstock. Proper blending is achieved by first pre-blending the catalyst precursor with a hydrocarbon diluent to form a diluted precursor mixture. For the following test studies, a hydrotreated heavy vacuum gas oil was used as the hydrocarbon diluent. The diluted precursor mixture was prepared such that 1 part by weight of the mixture could be added to 99 parts by weight of the heavy oil feedstock to achieve the target loading of dispersed metal sulfide catalyst in the conditioned feedstock. As a specific illustration, for a test study with a target loading of 30 ppm dispersed metal sulfide catalyst in the conditioned feedstock (where the loading is expressed based on metal concentration), the diluted precursor mixture was prepared with a 3000 ppm concentration of metal.

Note that for comparative test studies in which no dispersed metal sulfide catalyst was used, the hydrocarbon diluent (hydrotreated heavy vacuum gas oil) was added to the heavy oil feedstock at the same proportion of 1 part by weight of HVGO to 99 parts by weight of heavy oil feedstock. This ensured that the background composition was the same between tests using the dual catalyst system and those using only the heterogeneous (ebullated bed) catalyst, thereby allowing test results to be compared directly.

The heavy oil feedstock(s) and operating conditions for the actual tests are more particularly identified in the Examples below. The heterogeneous catalyst was a commercially available catalyst commonly used in ebullated bed reactors. The conditioned feedstock was recirculated out and back into the mixing vessel 502 by a pump 504, similar to a surge vessel and pump-around. A high precision positive displacement pump 506 was used to draw the conditioned feedstock from the recirculation loop and pressurize it to the reactor pressure. Hydrogen gas 508 was fed into the pressurized feedstock and the resulting mixture was passed through a pre-heater 510 prior to being introduced into first ebullated bed reactor 512.

Each ebullated bed reactor 512, 512' had an interior volume of about 3000 ml and included a mesh wire guard 514 to keep the heterogeneous catalyst within the reactor. Each reactor 512, 512' was also equipped with a recycle line 511, 511' and recycle pump 513, 513', which provided the required flow velocity in reactors to expand the heterogeneous catalyst bed. The combined volume of both reactors and their respective recycle lines, all of which were maintained at the specified reactor temperature, was 6,700 ml. This is the thermal reaction volume of the system, and was used as the basis for calculation of Liquid Hourly Space Velocity (LHSV).

In FIG. 5, a settled height of catalyst in each ebullated bed reactor 512, 512' is schematically indicated by a lower dotted line 516, and the expanded catalyst bed during use is schematically indicated by an upper dotted line 518. Upgraded material 520 from first reactor 512 was transferred together with supplemental hydrogen 508' into second reactor 512' for further hydroprocessing. The further upgraded material 520' from the second reactor 512' was introduced into a hot separator 522 to separate low-boiling hydrocarbon products and gases 524 from an unconverted liquid fraction (or separator bottoms) 526. The gases and hydrocarbon product vapors 524 were cooled and passed into a cold separator 528, where they were separated into gases 530 and converted hydrocarbon products, which were recovered as separator overheads 532.

The separator bottoms 526 were processed batch wise using a separate (i.e. offline) batch vacuum distillation apparatus 534. Dotted lines indicate batch wise processing, although it is within the scope of the disclosure to use continuous processing. Although vacuum distillation in a commercial unit would be performed in a continuous online distillation tower, batch distillation apparatus 534 was used for the purposes of the pilot plant tests. The batch distillation apparatus 534 processed 6000 g of the separator bottoms 526, with each batch being completed within a 6-hour period, and produced separator overheads 536 and a vacuum bottoms product 538. Batches were run at a pressure of about 1.5 mm Hg, allowing a 975° F. atmospheric equivalent end point to be reached at an actual pot temperature less than 650° F., thereby avoiding the onset of cracking reactions during the vacuum distillation.

Using the batch distillation apparatus 534, four vacuum distillation batches were completed each day, providing the required vacuum bottoms product for both analysis and recycling. For conditions involving recycling, the vacuum bottoms product 538 was recycled at 20% by volume of the fresh vacuum residue feed rate by recycling it into mixing device 502, where it was blended with the feedstock components 501.

EXAMPLE 1

The process used in Example 1 was a comparative example, for which the pilot plant described above was used with only a heterogeneous ebullated bed catalyst. For Example 1, no dispersed metal sulfide catalyst was used (meaning there was no dual catalyst system), and the process was operated without recycling of the vacuum bottoms to the ebullated bed reactor. The process was operated at a Liquid Hourly Space Velocity of 0.3 hr$^{-1}$ and a weighted average bed temperature (WABT) of 414° C. in both reactor stages. LHSV is defined as volume of fresh vacuum residue feedstock fed per hour per thermal reaction volume. Under these conditions, a vacuum residue conversion of about 55% was achieved, where conversion was defined based on a 538° C. (1000° F.) cut point.

A sample of the pilot plant separator bottoms product was subjected a laboratory distillation using the ASTM D-1160 method to obtain a 538° C.+vacuum residue product cut, which was analyzed for $C_7$ asphaltene content. $C_7$ asphaltene content was determined as the difference between the heptane insolubles and toluene insolubles contents of the sample.

Figure 6:
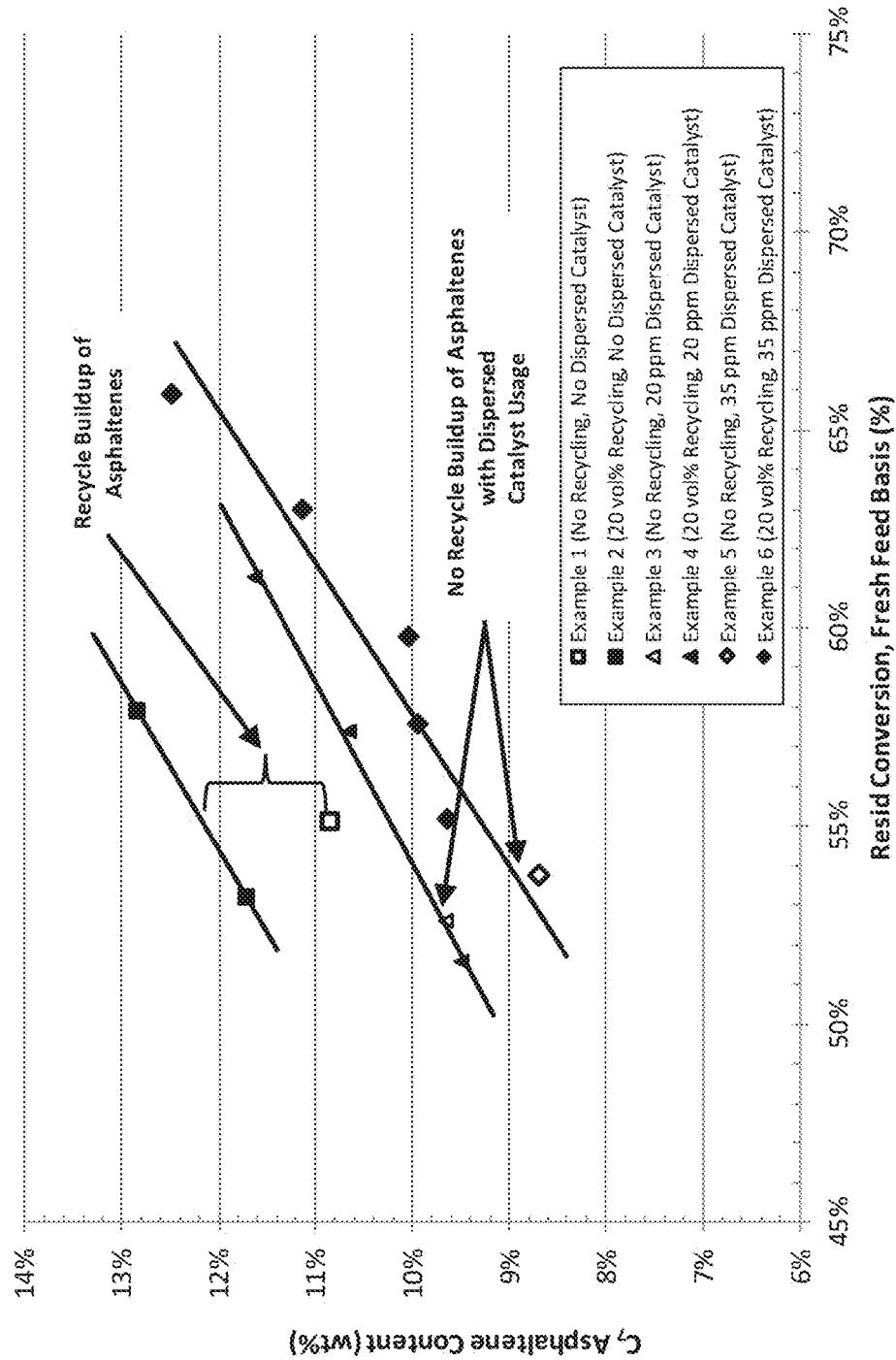
FIG. 6 is a line graph illustrating $C_7$ asphaltene content as a function of resid conversion for each of Examples 1-6, including at baseline conditions using heterogeneous catalyst and when operating upgraded ebullated bed reactor using a dual catalyst system.

The result of Example 1 is included in the chart of results shown in FIG. 6, and is depicted as an open square.

EXAMPLE 2

The process used in Example 2 was performed in the same way as in Example 1, except that the offline batch vacuum distillation apparatus was used to generate vacuum bottoms product, which was then recycled to the ebullated bed reactor as part of the process heavy oil feed. The batch vacuum distillation was operated with a 524° C. (975° F.) end point, and the resulting vacuum bottoms product was added to the ebullated bed process heavy oil feed at 20 vol % of the fresh vacuum residue feedstock. LHSV was maintained at 0.3 hr−1, noting that the definition of LHSV was based on fresh vacuum residue feed, as indicated in Example 1.

Data for Example 2 were collected at two different reactor temperatures (411° C. and 414° C.), resulting in a residue conversion of 53% and 58%, respectively. As described in Example 1, a sample of 538° C.+vacuum residue product was generated by laboratory D-1160 vacuum distillation and then characterized for $C_7$ asphaltene content. The results are shown in the chart of results shown in FIG. 6, and are depicted as solid squares connected by a line.

As seen in FIG. 6, at equal resid conversion, the process employed in Example 2 with recycling of vacuum bottoms results in a significantly higher $C_7$ asphaltene content than the process of Example 1, indicating a significant recycle buildup of harmful asphaltenes when recycling is used.

EXAMPLE 3

The process used in Example 3 was operated in the same way as in Example 2, except that dispersed metal sulfide catalyst was added to the heavy oil feed mixture. As noted above, the catalyst precursor was pre-dispersed in a hydrocarbon diluent (heavy vacuum gas oil), and then the premixed blend of catalyst precursor and hydrocarbon diluent (diluted catalyst precursor) was added to the vacuum residue feed oil. The catalyst precursor/hydrocarbon diluent was prepared such that an addition rate of 1 wt % of the fresh feed mix generated a dispersed catalyst concentration of 20 ppm by weight (as molybdenum).

The process was operated at a Liquid Hourly Space Velocity of 0.3 hr$^{-1}$ and a weighted average bed temperature (WABT) of 414° C. in both reactor stages. This resulted in a residue conversion of 52%. As previously, a sample of 538° C.+vacuum residue product was generated by laboratory D-1160 vacuum distillation and then characterized for $C_7$ asphaltene content.

The test result is shown in the chart of FIG. 6 as an open triangle. Relative to the result of Example 1 (open square), the asphaltene content is reduced due to the effect of the dispersed metal sulfide catalyst. As shown by the additional data from Example 4, the reduced asphaltene content was not simply the result of reduced conversion.

EXAMPLE 4

The process used in Example 4 was operated in the same way as in Example 2, with recycling of vacuum bottoms, except that dispersed metal sulfide catalyst was added to the feed mixture using the method of Example 3. The concentration of fresh dispersed catalyst was 20 ppm by weight (as molybdenum), based on the amount of fresh feed mix (vacuum residue plus dispersed catalyst/hydrocarbon diluent blend). The vacuum bottoms recycle stream also contained residual (used) dispersed metal sulfide catalyst, which was in addition to the fresh dispersed catalyst added to the heavy oil feed mix.

Data for Example 4 were collected at two different ebullated bed reactor temperatures (414° C. and 418° C.), resulting in residue conversion of 52% and 58%, respectively. As above, the 538° C.+vacuum residue product cut was generated by laboratory distillation and measured for $C_7$ asphaltene content. The results are shown in the chart of FIG. 6 as filled triangles connected by a line, which show a statistically linear relationship between asphaltene concentration and conversion, but with all points substantially lower than the results from Example 2.

In contrast to the results of Examples 1 and 2, which were obtained without the use of a dual catalyst system comprising a heterogeneous catalyst and a dispersed metal sulfide catalyst, the results of Example 4 with 20 ppm dispersed metal sulfide catalyst and recycling of vacuum bottoms overlap the result of Example 3 without recycling. This means that the use of 20 ppm dispersed catalyst prevented recycle buildup of asphaltenes. When used in combination with recycling of vacuum bottoms, the dispersed catalyst provides a double benefit: (1) the baseline asphaltene content (without recycling) is (or can be) reduced; and (2) recycle buildup of asphaltenes is prevented when recycling vacuum bottoms back to the ebullated bed reactor.

EXAMPLE 5

The process used in Example 5 was operated in the same way as in Example 3, except that the concentration of dispersed metal sulfide catalyst concentration was increased to 35 ppm by weight (as molybdenum). The process was operated with an average ebullated bed temperature of 415° C. in both reactor stages, resulting in a residue conversion of 54%.

The resulting $C_7$ asphaltene content of the lab-generated vacuum residue product cut is shown in the chart in FIG. 6 as an open diamond. The result of Example 5 at 35 ppm dispersed metal sulfide catalyst showed a further reduction in asphaltene content and at higher conversion compared to the result in Example 3 at 20 ppm.

EXAMPLE 6

The process used in Example 6 was operated in the same way as Example 4, except that the dispersed metal sulfide catalyst concentration was increased to 35 ppm by weight (as molybdenum). The process was operated with average ebullated bed temperatures of 415° C., 418° C., 420° C., and 425° C., resulting in residue conversions of 55%, 59%, 62%, and 66%, respectively.

The resulting $C_7$ asphaltene contents of the corresponding lab-generated vacuum residue product cuts are shown in the chart in FIG. 6 as filled diamonds connected by a best fit line. Similar to the results of Examples 3 and 4, the results of Example 6 overlap with that of Example 5, showing that the dispersed metal sulfide catalyst prevented the recycle buildup of asphaltenes, in addition to reducing the background level of asphaltenes without recycling of vacuum bottoms.

EXAMPLE 7

Figure 7:
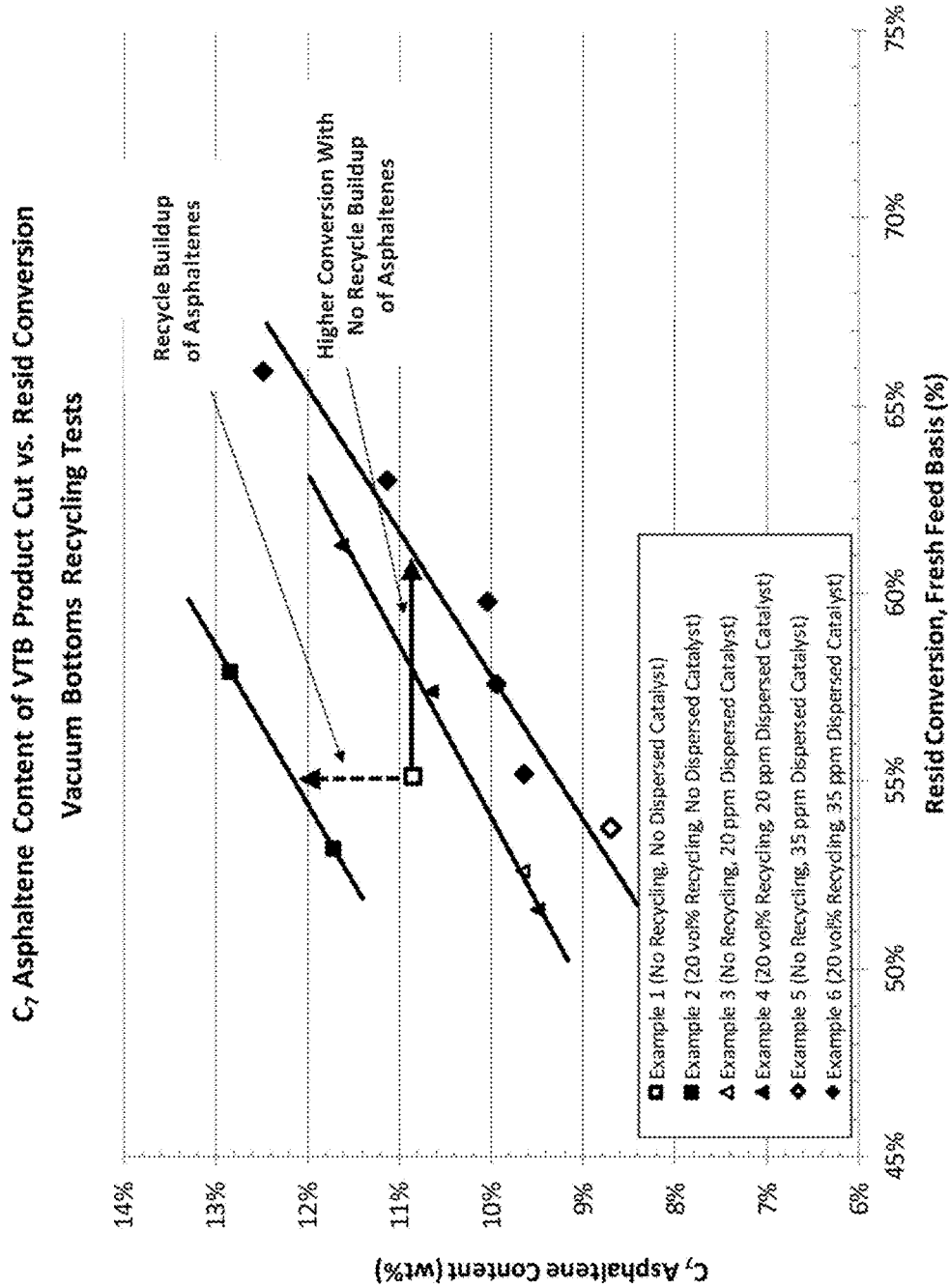
FIG. 7 is a line graph illustrating embodiments in which an upgraded ebullated bed reactor using a dual catalyst system is operated at higher conversion compared to baseline conditions without recycle buildup of asphaltenes in the vacuum bottoms.

With reference to the chart of FIG. 7 and exemplified by the process illustrated in FIG. 3B, an upgraded ebullated bed reactor using a dual catalyst system with recycling of vacuum bottoms can be operated at higher conversion with no recycle buildup of asphaltenes, as shown by the solid horizontal arrow extending to the right of the open square. This is in contrast to the broken vertical arrow extending above the open square where recycling of vacuum bottoms increased asphaltene concentration at equal conversion.

The addition of the dispersed metal sulfide catalyst to create a dual catalyst system allows resid conversion to be increased while maintaining equal asphaltene concentration, which results in: (1) increased rate of production of converted products while (2) avoiding or reducing the risk of increased process or equipment fouling and (3) maintaining bottoms product quality.

This embodiment is favorable when baseline process fouling is manageable and the economic benefit is most favorable for increasing the rate of production of converted products.

EXAMPLE 8

Figure 8:
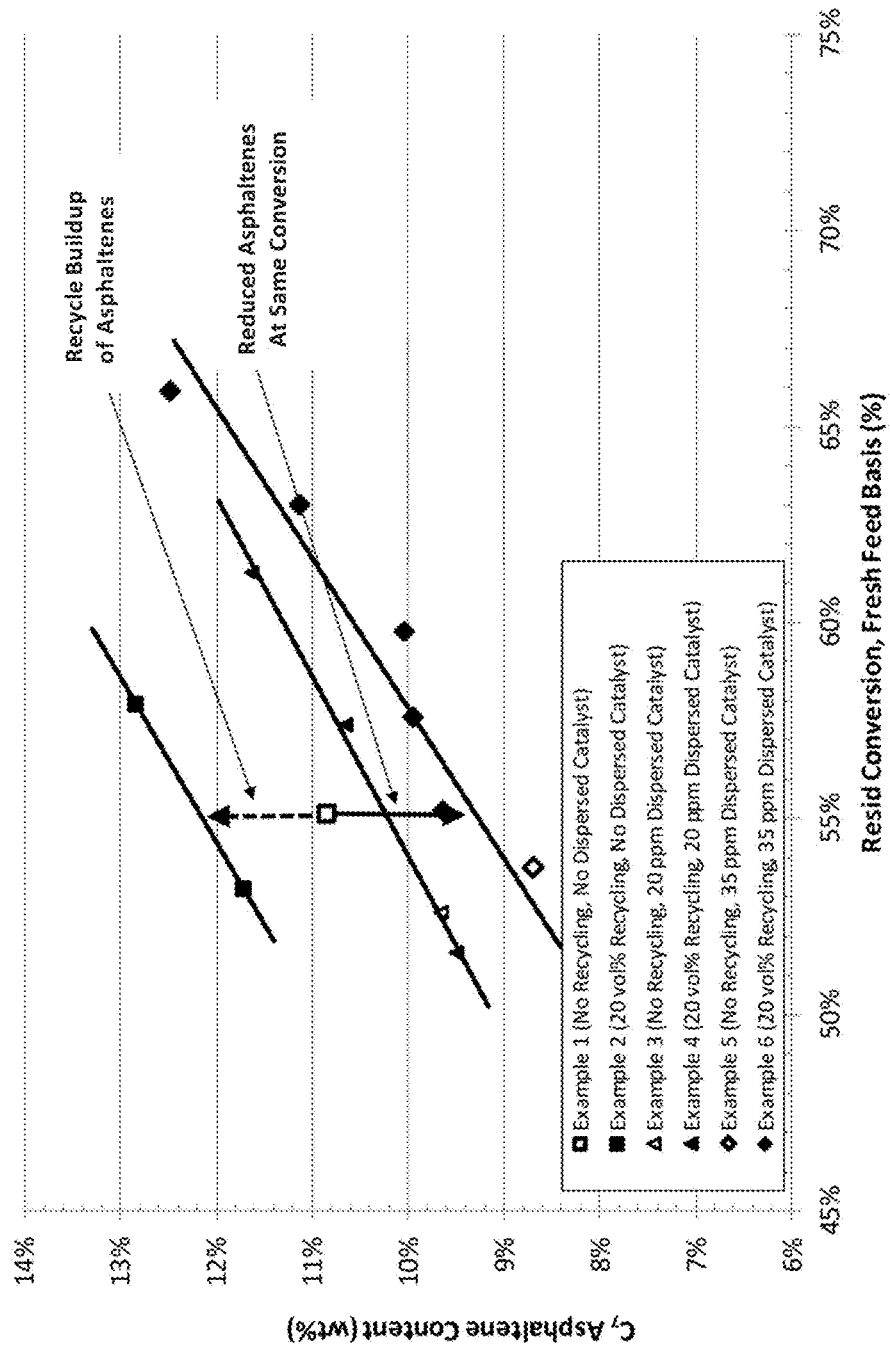
FIG. 8 is a line graph illustrating embodiments in which an upgraded ebullated bed reactor using a dual catalyst system is operated at similar conversion compared to baseline conditions with reduced asphaltenes in the vacuum bottoms.

With reference to the chart of FIG. 8 and exemplified by the process illustrated in FIG. 3C, an upgraded ebullated bed reactor using a dual catalyst system with recycling of vacuum bottoms can be operated at similar conversion and with a substantial reduction in asphaltene concentration, as shown by the solid vertical arrow extending below the open square. This is in contrast to the broken vertical arrow extending above the open square where recycling of vacuum bottoms increased asphaltene concentration at equal conversion.

The addition of the dispersed metal sulfide catalyst to create a dual catalyst system allows resid conversion to be maintained while reducing asphaltene concentration, which results in: (1) maintaining the same rate of production of converted products while (2) reducing process or equipment fouling and (3) improving bottoms product quality.

This embodiment is favorable when baseline process fouling and/or bottoms product quality are limiting so that the economic benefit is maximized by reducing fouling and/or improving bottoms product quality.

EXAMPLE 9

Figure 9:
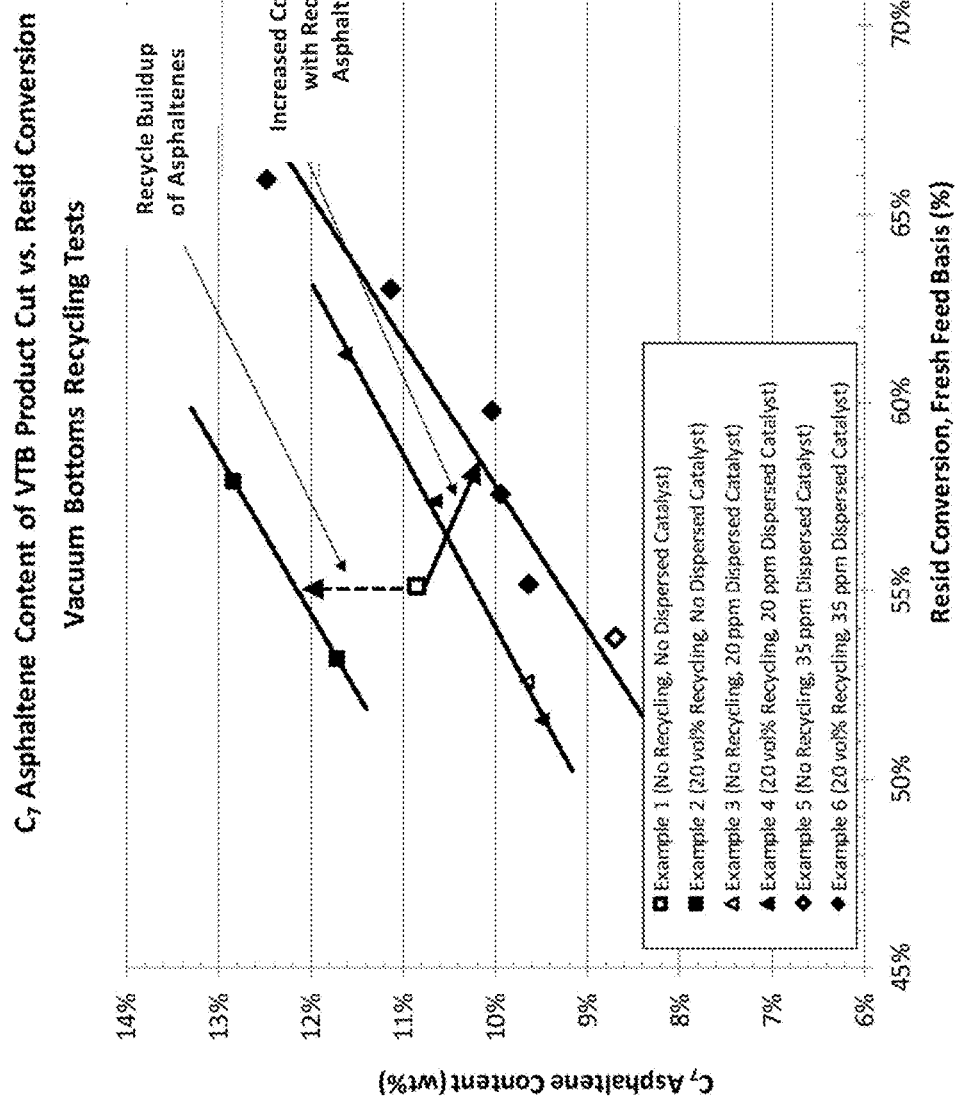
FIG. 9 is a line graph illustrating embodiments in which an upgraded ebullated bed reactor using a dual catalyst system is operated at higher conversion compared to baseline conditions with reduced asphaltenes in the vacuum bottoms.

With reference to the chart of FIG. 9 and exemplified by the process illustrated in FIG. 3D, an upgraded ebullated bed reactor using a dual catalyst system with recycling of vacuum bottoms can be operated at higher conversion and with a reduction in asphaltene concentration, as shown by the solid vertical arrow extending diagonally to the right and below the open square. This is in contrast to the broken vertical arrow extending above the open square where recycling of vacuum bottoms increased asphaltene concentration at equal conversion.

The addition of the dispersed metal sulfide catalyst to create a dual catalyst system allows resid conversion to be increased while and asphaltene concentration to be reduced, which results in: (1) increased rate of production of converted products, albeit to a lesser extent than in Example 7, while (2) reducing process or equipment fouling and (3) improving bottoms product quality, but to a lesser extent than in Example 8.

This embodiment allows the benefits to be balanced in a way that optimizes the overall economic performance of the process. The illustration in this example indicates a case where the production improvement is relatively more valuable than the reduction in process fouling and/or improvement in bottoms product quality.

EXAMPLE 10

Figure 10:
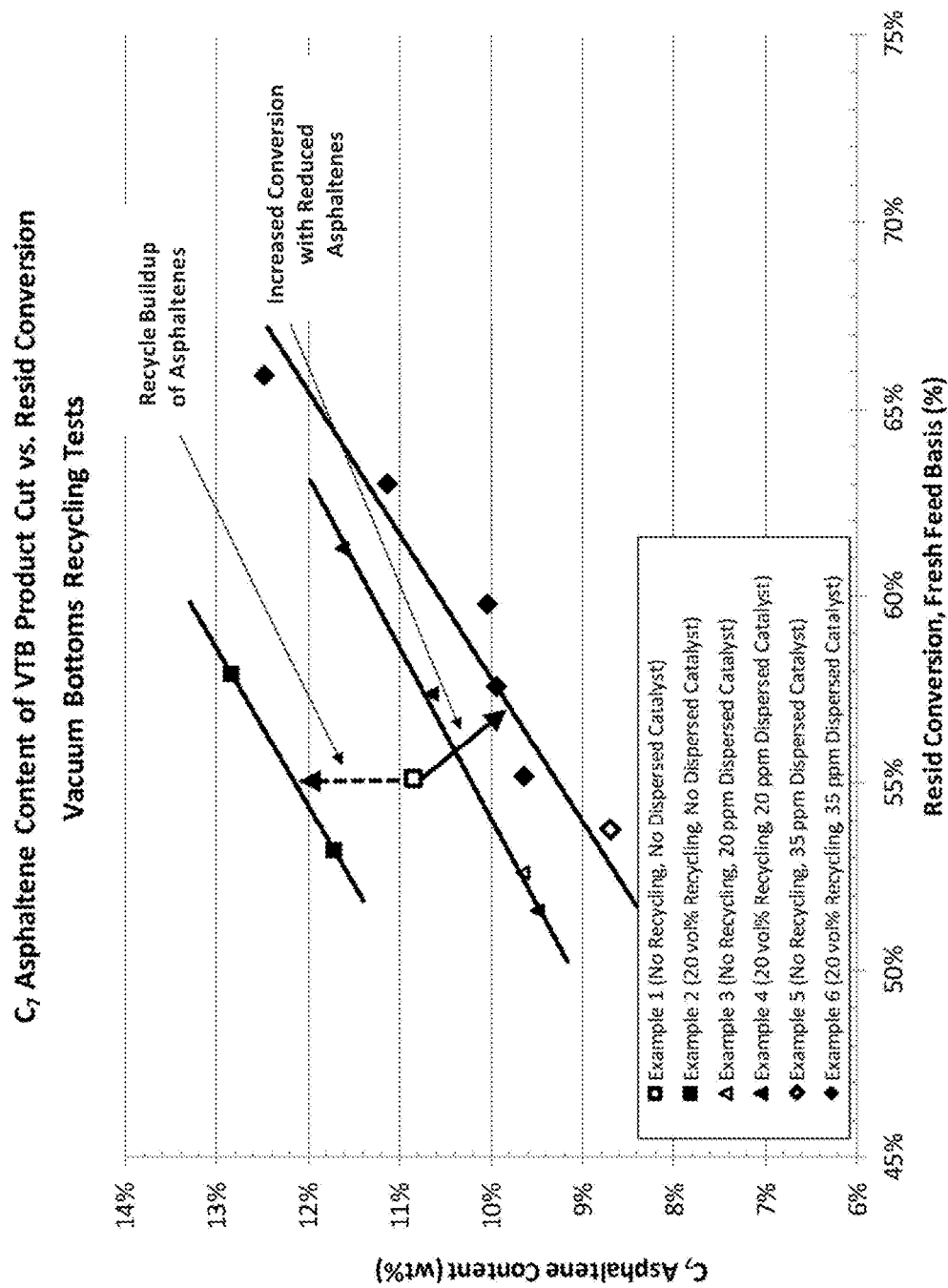
FIG. 10 is a line graph illustrating other embodiments in which an upgraded ebullated bed reactor using a dual catalyst system is operated at higher conversion compared to baseline conditions with reduced asphaltenes in the vacuum bottoms.
Figure 2B:
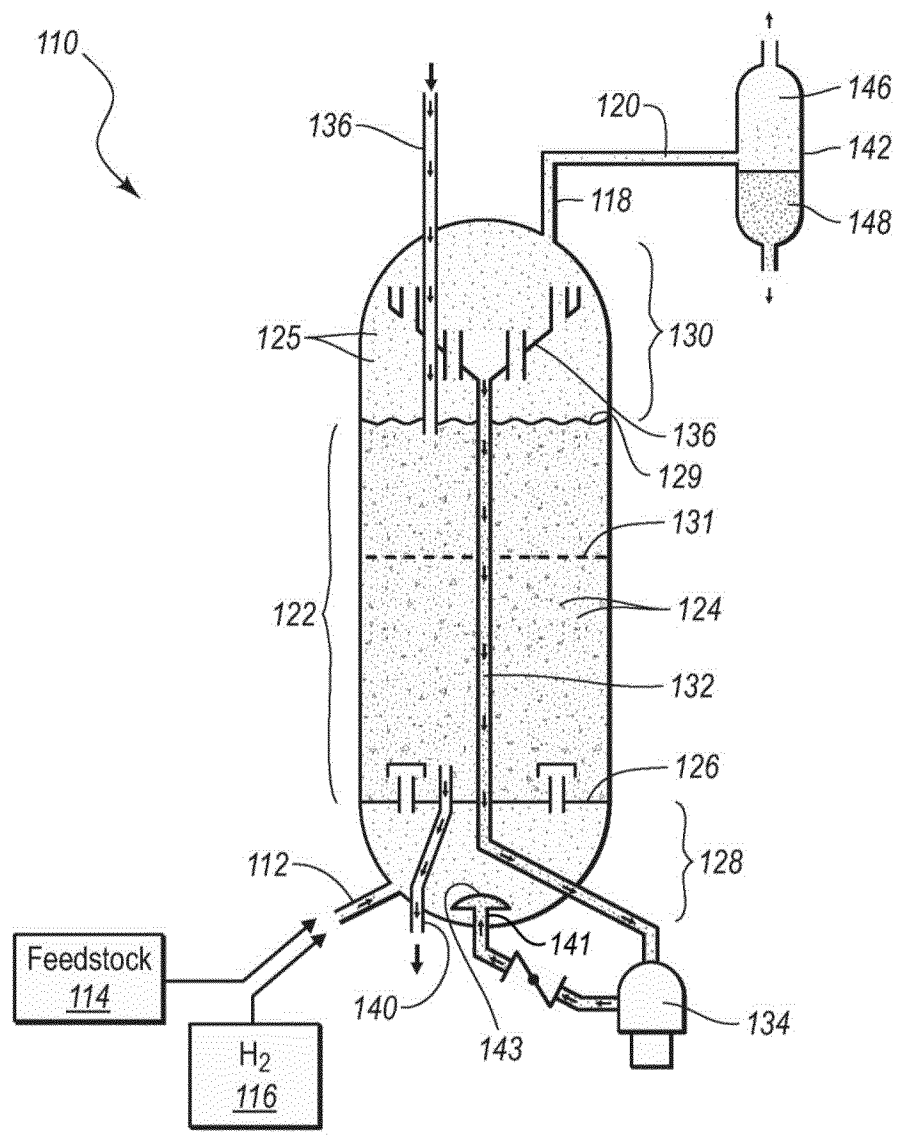

With reference to the chart of FIG. 10 and exemplified by the process illustrated in FIG. 3D, an upgraded ebullated bed reactor using a dual catalyst system with recycling of vacuum bottoms can be operated at higher conversion and with a reduction in asphaltene concentration, as shown by the solid vertical arrow extending diagonally to the right and below the open square. This is in contrast to the broken vertical arrow extending above the open square where recycling of vacuum bottoms increased asphaltene concentration at equal conversion.

The addition of the dispersed metal sulfide catalyst to create a dual catalyst system allows resid conversion to be increased and asphaltene concentration to be reduced, which results in: (1) increased rate of production of converted products, albeit to a lesser extent than in Examples 7 and 9, while (2) reducing process or equipment fouling and (3) improving bottoms product quality, albeit to a lesser extent than in Example 8 but to a greater extent than in Example 9.

Compared to Example 9, this embodiment illustrates a case where the reduction in process fouling and/or improvement in bottoms product quality are relatively more economically valuable than the increased rate of production of converted products.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of upgrading an ebullated bed hydroprocessing system that includes one or more ebullated bed reactors with recycling vacuum bottoms and without recycle buildup of asphaltenes, comprising:
    operating an ebullated bed reactor using a heterogeneous catalyst to hydroprocess heavy oil at baseline conditions, optionally with recycling of vacuum bottoms and recycle buildup of asphaltenes, the baseline conditions including severity, which is related to operating temperature, throughput, and conversion;
    adding or forming in situ dispersed metal sulfide catalyst particles in the ebullated bed reactor to yield an upgraded ebullated bed reactor with a dual catalyst system comprised of heterogeneous catalyst and dispersed metal sulfide catalyst particles;
    operating the upgraded ebullated bed reactor using the dual catalyst system at same or higher severity than when operating the ebullated bed reactor at the baseline conditions to hydroprocess heavy oil to produce hydrocarbon products;
    subjecting the hydrocarbon products to one or more separation processes including vacuum distillation and separating distillates from vacuum bottoms containing residual metal sulfide catalyst particles; and
    recycling at least a portion of the vacuum bottoms containing residual metal sulfide catalyst particles into the upgraded ebullated bed reactor without recycle buildup of asphaltenes in the ebullated bed hydroprocessing system, the vacuum bottoms being recycled at a recycle ratio of from 1% to 50% based on the flow rate of recycled vacuum bottoms as a volume percent of the flow rate of fresh heavy oil added to the upgraded ebullated bed reactor and such that said recycling does not increase asphaltene concentration in the upgraded ebullated bed reactor and/or the vacuum bottoms.

2. The method of claim 1, wherein operating the upgraded ebullated bed reactor includes operating at higher conversion than the conversion at the baseline conditions and without causing recycle buildup of asphaltenes in the vacuum bottoms.

3. The method of claim 2, wherein the higher conversion is selected so as to increase the rate of production of converted products compared to at the baseline conditions without increasing equipment fouling and without reducing bottoms product quality.

4. The method of claim 1, wherein operating the upgraded ebullated bed reactor includes operating at similar conversion as the conversion at the baseline conditions and with reduced concentration of asphaltenes in the vacuum bottoms.

5. The method of claim 1, wherein operating the upgraded ebullated bed reactor at similar conversion maintains the rate of production of converted products compared to at the baseline conditions while decreasing equipment fouling and improving bottoms product quality.

6. The method of claim 1, wherein operating the upgraded ebullated bed reactor includes operating at higher conversion and increased rate of production of converted products than the conversion and rate of production of converted products at the baseline conditions and with reduced concentration of asphaltenes in the vacuum bottoms and while improving bottoms product quality.

7. The method of claim 1, wherein the vacuum bottoms is recycled at a recycle ratio of from about 5% to about 40% based on the flow rate of recycled vacuum bottoms as a volume percent of the flow rate of fresh heavy oil added to the upgraded ebullated bed reactor.

8. The method of claim 1, wherein operating the upgraded ebullated bed reactor using the dual catalyst system is performed at similar or higher temperature compared to the baseline conditions.

9. The method of claim 1, wherein operating the upgraded ebullated bed reactor using the dual catalyst system is performed at similar or higher conversion compared to the baseline conditions.

10. The method of claim 1, wherein operating the upgraded ebullated bed reactor using the dual catalyst system is performed at similar or higher throughput than compared to the baseline conditions.

11. The method of claim 1, wherein operating the upgraded ebullated bed reactor using the dual catalyst system includes hydroprocessing heavy oil having lower quality, such as having a higher asphaltene concentration, compared to when hydroprocessing heavy oil at the baseline conditions.

12. The method of claim 11, wherein the asphaltene concentration of the lower quality heavy oil is at least 2% higher than the asphaltene concentration of the heavy oil when operating at the baseline conditions.

13. The method of claim 11, wherein the upgraded ebullated bed reactor hydroprocesses asphaltene with increased conversion of at least 2% compared to asphaltene conversion at the baseline conditions.

14. The method of claim 1, wherein operating the upgraded ebullated bed reactor results in a rate of equipment fouling that is no higher or that is lower than a rate of equipment fouling when operating at the baseline conditions, wherein the rate of equipment fouling is determined by at least one of:
(i) frequency of required heat exchanger clean-outs;
(ii) frequency of switching to spare heat exchangers;
(iii) frequency of filter changes;
(iv) frequency of strainer clean-outs or changes;
(v) rate of decrease in equipment skin temperatures, including in equipment selected from heat exchangers, separators, or distillation towers;
(vi) rate of increase in furnace tube metal temperatures;
(vii) rate of increase in calculated fouling resistance factors for heat exchangers and furnaces;
(viii) rate of increase in differential pressure of heat exchangers;
(ix) frequency of cleaning atmospheric and/or vacuum distillation towers; or
(x) frequency of maintenance turnarounds.

15. The method of claim 14, wherein operating the upgraded ebullated bed reactor using the dual catalyst system and recycling at least a portion of the vacuum bottoms reduces the rate of equipment fouling by at least 25% compared to the rate of equipment fouling at the baseline conditions.

16. The method of claim 1, wherein the heavy oil comprises at least one of heavy crude oil, oil sands bitumen, residuum from refinery processes, atmospheric tower bottoms having a nominal boiling point of at least 343° C. (650° F.), vacuum tower bottoms having a nominal boiling point of at least 524° C. (975° F.), resid from a hot separator, resid pitch, resid from solvent extraction, or vacuum residue.

17. The method of claim 1, wherein the dispersed metal sulfide catalyst particles are less than 1 μm in size.

18. The method of claim 1, wherein upgrading the ebullated bed reactor to operate using a dual catalyst system includes forming the dispersed metal sulfide catalyst particles in situ within the heavy oil from a catalyst precursor, wherein forming the dispersed metal sulfide catalyst particles in situ within the heavy oil comprises mixing the catalyst precursor with a diluent hydrocarbon to form a diluted precursor mixture, blending the diluted precursor mixture with the heavy oil to form conditioned heavy oil, and heating the conditioned heavy oil to decompose the catalyst precursor and form the dispersed metal sulfide catalyst particles in situ within the heavy oil.

19. A method of upgrading an ebullated bed hydroprocessing system that includes one or more ebullated bed reactors with recycling vacuum bottoms, with increased conversion, and without recycle buildup of asphaltenes, comprising:
operating an ebullated bed reactor using a heterogeneous catalyst to hydroprocess heavy oil at baseline conditions, optionally with recycling of vacuum bottoms and recycle buildup of asphaltenes, the baseline conditions including severity, which is related to operating temperature, throughput, and conversion;
adding or forming in situ dispersed metal sulfide catalyst particles in the ebullated bed reactor to yield an upgraded ebullated bed reactor with a dual catalyst system comprised of heterogeneous catalyst and dispersed metal sulfide catalyst particles;
operating the upgraded ebullated bed reactor using the dual catalyst system to hydroprocess heavy oil to produce hydrocarbon products at higher conversion compared to the conversion when operating the ebullated bed reactor at the baseline conditions;
subjecting the hydrocarbon products to one or more separation processes including vacuum distillation and separating distillates from vacuum bottoms containing residual metal sulfide catalyst particles; and
recycling at least a portion of the vacuum bottoms containing residual metal sulfide catalyst particles into the upgraded ebullated bed reactor without recycle buildup of asphaltenes in the vacuum bottoms, the vacuum bottoms being recycled at a recycle ratio of from 1% to 50% based on the flow rate of recycled vacuum bottoms as a volume percent of the flow rate of fresh heavy oil added to the upgraded ebullated bed reactor and such that said recycling does not increase asphaltene concentration in the vacuum bottoms.

20. The method of claim 19, wherein conversion is increased when operating the upgraded ebullated bed reactor using the dual catalyst system by at least 5% compared to the conversion when operating the ebullated bed reactor at the baseline conditions.

21. The method of claim 19, wherein operating the upgraded ebullated bed reactor at higher conversion increases the rate of production of converted products compared to baseline conditions without increasing equipment fouling and without reducing bottoms product quality.

22. A method of upgrading an ebullated bed hydroprocessing system that includes one or more ebullated bed reactors with recycling vacuum bottoms, with similar conversion, and with reduced asphaltene concentration, comprising:
operating an ebullated bed reactor using a heterogeneous catalyst to hydroprocess heavy oil at baseline conditions, optionally with recycling of vacuum bottoms and recycle buildup of asphaltenes, the baseline conditions including severity, which is related to operating temperature, throughput, and conversion;
adding or forming in situ dispersed metal sulfide catalyst particles in the ebullated bed reactor to yield an upgraded ebullated bed reactor with a dual catalyst system comprised of heterogeneous catalyst and dispersed metal sulfide catalyst particles;
operating the upgraded ebullated bed reactor using the dual catalyst system to hydroprocess heavy oil to produce hydrocarbon products at similar conversion compared to the conversion when operating the ebullated bed reactor at the baseline conditions;
subjecting the hydrocarbon products to one or more separation processes including vacuum distillation and separating distillates from vacuum bottoms containing residual metal sulfide catalyst particles; and recycling at least a portion of the vacuum bottoms containing residual metal sulfide catalyst particles into the upgraded ebullated bed reactor with reduced asphaltenes in the vacuum bottoms, the vacuum bottoms being recycled at a recycle ratio of from 1% to 50% based on the flow rate of recycled vacuum bottoms as a volume percent of the flow rate of fresh heavy oil added to the upgraded ebullated bed reactor and such that said recycling reduces asphaltene concentration in the vacuum bottoms.

23. The method of claim 22, wherein operating the upgraded ebullated bed reactor at similar conversion maintains the rate of production of converted products compared to at the baseline conditions while decreasing equipment and/or process fouling and while improving bottoms product quality.

24. A method of upgrading an ebullated bed hydroprocessing system that includes one or more ebullated bed reactors with recycling vacuum bottoms, with increased conversion, and with reduced asphaltene concentration, comprising:

operating an ebullated bed reactor using a heterogeneous catalyst to hydroprocess heavy oil at baseline conditions, optionally with recycling of vacuum bottoms and recycle buildup of asphaltenes, the baseline conditions including severity, which is related to operating temperature, throughput, and conversion;

adding or forming in situ dispersed metal sulfide catalyst particles in the ebullated bed reactor to yield an upgraded ebullated bed reactor with a dual catalyst system comprised of heterogeneous catalyst and dispersed metal sulfide catalyst particles;

operating the upgraded ebullated bed reactor using the dual catalyst system to hydroprocess heavy oil to produce hydrocarbon products at higher conversion compared to the conversion when operating the ebullated bed reactor at the baseline conditions;

subjecting the hydrocarbon products to one or more separation processes including vacuum distillation and separating distillates from vacuum bottoms containing residual metal sulfide catalyst particles; and recycling at least a portion of the vacuum bottoms containing residual metal sulfide catalyst particles into the upgraded ebullated bed reactor with reduced asphaltenes in the vacuum bottoms, the vacuum bottoms being recycled at a recycle ratio of from 1% to 50% based on the flow rate of recycled vacuum bottoms as a volume percent of the flow rate of fresh heavy oil added to the upgraded ebullated bed reactor and such that said recycling reduces asphaltene concentration in the vacuum bottoms.

25. The method of claim 24, wherein operating the upgraded ebullated bed reactor at higher conversion increases the rate of production of converted products compared to at the baseline conditions while decreasing equipment fouling and while improving bottoms product quality.

* * * * *

UNITED STATES PATENT AND TRADEMARK OFFICE
CERTIFICATE OF CORRECTION

PATENT NO. : 11,091,707 B2  
APPLICATION NO. : 16/594847  
DATED : August 17, 2021  
INVENTOR(S) : Michael A. Rueter et al.

Page 1 of 3

It is certified that error appears in the above-identified patent and that said Letters Patent is hereby corrected as shown below:

On the Title Page

Page 4
Item (56), References Cited, Other Publications, change "Panariti et al.: "Petroleum Residue Upgrading with Dispered Catalysts Part 1. Activity and Selctivity" Applied Catalysts A: General, vol.204, Mar. 31, 2000 (Mar. 1, 2000) pp. 203-213." to –Panariti et al.: "Petroleum Residue Upgrading with Dispersed Catalysts Part 1. Activity and Selectivity" Applied Catalysts A: General, vol.204, Mar. 31, 2000 (Mar. 1, 2000) pp. 203-213.–

Page 5
Item (56), References Cited, Other Publications, change "N. Panariti et al.: "petroleum Residue Upgrading with Dispered Catalyst Part 1. Catalyst Activity and Selctivity" Applied Catalysts A: General, vol. 204, Mar. 31, 2000 (Mar. 1, 2000) pp. 203-213." to –N. Panariti et al.: "petroleum Residue Upgrading with Dispersed Catalyst Part 1. Catalyst Activity and Selectivity" Applied Catalysts A: General, vol. 204, Mar. 31, 2000 (Mar. 1, 2000) pp. 203-213.–

In the Drawings

Sheet 3, replace Fig. 2B with the attached replacement drawing where reference number 141 is added In the Specification Column 5
Line 47, change "such the" to –such as the–

Column 13
Line 57, change "inlet tube 137" to –inlet tube 136–

Column 18
Line 16, change "30$" to –30%–

Signed and Sealed this  
Twenty-eighth Day of December, 2021

Drew Hirshfeld  
*Performing the Functions and Duties of the  
Under Secretary of Commerce for Intellectual Property and  
Director of the United States Patent and Trademark Office*

Column 31
Line 11, after "increased" delete "while"